(12) United States Patent
Mahmood et al.

(10) Patent No.: US 11,956,362 B2
(45) Date of Patent: *Apr. 9, 2024

(54) CENTRALIZED AND DECENTRALIZED INDIVIDUALIZED MEDICINE PLATFORM

(71) Applicant: Janssen Biotech, Inc., Horsham, PA (US)

(72) Inventors: Khurram Mahmood, San Ramon, CA (US); Eric Matthew Bell, Emeryville, CA (US); Stuart Maxwell Altman, El Cerrito, CA (US); Jeremy Alan Dunn, Oakland, CA (US); Sambasiva R. Pedapalli, San Ramon, CA (US); Christopher Prado Dunn, San Francisco, CA (US); Nerses Ohanyan, North Hollywood, CA (US); Anand Kothari, Cupertino, CA (US); Ryan Jeffrey Southwick, Pacifica, CA (US); Richard Brewster Wickersham, III, San Francisco, CA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/586,644

(22) Filed: Jan. 27, 2022

(65) Prior Publication Data

US 2022/0294628 A1 Sep. 15, 2022

Related U.S. Application Data

(63) Continuation of application No. 16/698,553, filed on Nov. 27, 2019, now Pat. No. 11,271,741.

(Continued)

(51) Int. Cl.
*H04L 29/06* (2006.01)
*G16H 20/00* (2018.01)
(Continued)

(52) U.S. Cl.
CPC .......... *H04L 9/3213* (2013.01); *G16H 20/00* (2018.01); *H04L 9/0637* (2013.01); *H04L 63/102* (2013.01); *H04L 9/50* (2022.05)

(58) Field of Classification Search
CPC ... H04L 9/3213; H04L 9/0637; H04L 63/102; H04L 2209/38; H04L 2209/88; H04L 9/3239; G16H 20/00; G16H 40/20
See application file for complete search history.

(56) References Cited

U.S. PATENT DOCUMENTS

| | | |
|---|---|---|
| 7,774,243 B1 | 8/2010 | Antony et al. |
| 10,244,965 B1 | 4/2019 | Gibson |

(Continued)

FOREIGN PATENT DOCUMENTS

| | | |
|---|---|---|
| WO | 2001024771 A1 | 4/2001 |
| WO | 2012099973 A2 | 7/2012 |

(Continued)

OTHER PUBLICATIONS

Levine et al., "Global Manufacturing of CAR T Cell Therapy," Molecular Therapy: Methods & Clinical Development vol. 4 Mar. 2017, pp. 92-101.

(Continued)

*Primary Examiner* — Mahfuzur Rahman
(74) *Attorney, Agent, or Firm* — Goodwin Procter LLP

(57) ABSTRACT

The subject disclosure relates to systems, devices, and methods for executing operations related to procurement of individualized medicine therapies. Also disclosed are embodiments systems, methods, and devices for accessing a wide range of individualized medicine platform modules. Furthermore, disclosed herein are individualized medicine platform systems, methods and devices communicatively coupled to blockchain computing systems comprising several nodes. The disclosed systems, methods, and devices (Continued)

also generate chain of custody and chain of identity event data.

29 Claims, 11 Drawing Sheets

Related U.S. Application Data

(60) Provisional application No. 62/772,955, filed on Nov. 29, 2018.

(51) Int. Cl.
    *H04L 9/06*     (2006.01)
    *H04L 9/32*     (2006.01)
    *H04L 9/40*     (2022.01)
    *H04L 9/00*     (2022.01)

(56) References Cited

U.S. PATENT DOCUMENTS

| | | |
|---|---|---|
| 10,817,949 B1 | 10/2020 | Wieduwilt et al. |
| 2002/0187526 A1 | 12/2002 | Ruben et al. |
| 2006/0172422 A1 | 8/2006 | Dzekunov et al. |
| 2014/0136259 A1 | 5/2014 | Kinsey et al. |
| 2014/0297311 A1* | 10/2014 | Jackson ............. G06Q 30/0201 705/2 |
| 2017/0039330 A1 | 2/2017 | Tanner et al. |
| 2017/0220964 A1* | 8/2017 | Datta Ray ......... G06Q 10/0635 |
| 2017/0364637 A1* | 12/2017 | Kshepakaran ......... G16H 10/60 |
| 2018/0096175 A1 | 4/2018 | Schmeling et al. |
| 2018/0096347 A1 | 4/2018 | Goeringer et al. |
| 2018/0264347 A1 | 9/2018 | Tran et al. |
| 2018/0336554 A1 | 11/2018 | Trotter |
| 2019/0012666 A1 | 1/2019 | Krauss et al. |
| 2019/0088373 A1 | 3/2019 | Sarmentero |
| 2019/0096534 A1 | 3/2019 | Joao |
| 2019/0214116 A1 | 7/2019 | Eberting |
| 2019/0214119 A1* | 7/2019 | Wachira ................. G16H 20/10 |
| 2020/0058381 A1 | 2/2020 | Patel |
| 2020/0167725 A1 | 5/2020 | Bolene et al. |
| 2020/0179230 A1 | 6/2020 | Molloy et al. |
| 2020/0258605 A1 | 8/2020 | Blechman |
| 2020/0364588 A1 | 11/2020 | Knox |
| 2021/0110897 A1 | 4/2021 | Ginsburg et al. |
| 2021/0280287 A1 | 9/2021 | Mahmood et al. |

FOREIGN PATENT DOCUMENTS

| | | |
|---|---|---|
| WO | 2015142675 A2 | 9/2015 |
| WO | 2017079703 A1 | 5/2017 |
| WO | 2017096327 A2 | 6/2017 |
| WO | 2017117112 A1 | 7/2017 |
| WO | 2018187332 A1 | 10/2018 |
| WO | 2019055896 A1 | 3/2019 |

OTHER PUBLICATIONS

Olweus J. (2017). Manufacture of CAR-T cells in the body. Nature biotechnology, 35(6), pp. 520-521. https://doi.org/10.1038/nbt.3898.

Merhavi-Shoham et al., "Adoptive Cell Therapy for Metastatic Melanoma," The Cancer Journal, vol. 23, No. 1, Jan./Feb. 2017, pp. 48-53.

Kochenderfer et al., "Lymphoma Remissions Caused by Anti-CD19 Chimeric Antigen Receptor T Cells are Associated With High Serum Interleukin-15 Levels," J Clin Oncol. Jun. 1, 2017;35(16):1803-1813. doi: 10.1200/JCO.2016.71.3024. Epub Mar. 14, 2017. PMID: 28291388; PMCID: PMC5455597.

Vineti Inc., Product Data Sheet, www.vineti.com, 2021, 2 pages.

Vineti, Inc., "Cell and Gene Therapy, Supply Chain Management: Readiness Checklist," 2021, 4 pages.

Vineti, Inc., "Chain of Identify (COI) Identifier, An industry standard recommendation for personalized therapeutics, as presented to the Standards Coordinating Body for Regenerative Medicine," Oct. 2020, 15 pages.

Vineti, Inc., "Personalized Supply Chain Strategies, A Supply Chain Readiness Guide for cell therapies, gene therapies, and personalized cancer vaccines," 2020, 22 pages.

PCT/US2019/63747—International Search Report dated Mar. 10, 2020, 2 pages.

\* cited by examiner

CENTRALIZED AND DECENTRALIZED INDIVIDUALIZED MEDICINE PLATFORM

CROSS-REFERENCE TO RELATED APPLICATION(S)

This application is a continuation of U.S. patent application Ser. No. 16/698,553 titled "CENTRALIZED AND DECENTRALIZED INDIVIDUALIZED MEDICINE PLATFORM", filed Nov. 27, 2019, now U.S. Pat. No. 11,271,741, which claims priority to U.S. Patent Application No. 62/772,955 titled, "CENTRALIZED AND DECENTRALIZED INDIVIDUALIZED MEDICINE PLATFORM", filed Nov. 29, 2018. The entirety of the disclosures of the aforementioned applications are considered part of, and are incorporated by reference in, the disclosure of this application.

BACKGROUND

The recent emergence in disease prevention and treatment known as precision medicine offers several benefits to patients. This approach to medicine allows for the provisioning of customized therapies to patients based on calculated predictions of which treatments may work best for a particular patient. For instance, CAR-T cell therapy is a cancer treatment that involves the extraction of T-cells from a patient's blood and modifying the cell surface to include chimeric antigen receptors that facilitate the production of a chemical to attack tumor cells. Although, these treatments are revolutionizing disease treatment, a complex chain of processes must be undertaken in order to generate the therapeutics ultimately administered to the patient.

For instance, the process begins with the extraction of a patient blood sample which are sometimes transported to storage facilities before arriving at a manufacturing facility. Once the patient-tailored therapeutic is manufactured, the therapeutic is transported back to a facility employing staff that can infuse the therapeutic medicine (e.g., manufactured CAR-T cells) into the patient system. This generalized overview of various points along a personalized medicine supply chain is fraught with logistical challenges, scheduling challenges, stakeholder coordination challenges, monitoring and tracking challenges, and other related problems.

For instance, the supply chain continues to operate inefficiently in that several stakeholders including medical personnel, patients, providers, centers of excellence (e.g., hospital or laboratories), manufacturing facilities, couriers, administrative staff, and other such stakeholders do not coordinate activities in a manner that ensures chain of identity and chain of custody of materials (e.g., patient sample), intermediary products, and end products (e.g., therapeutic drug) are accounted for at all points along the supply chain and at all times. Other challenges include the coordination of sending samples used in manufacturing therapies to manufacturing facilities having a capacity to perform manufacturing activities at a given time.

The scheduling of patient sample extraction activities, timing of couriers to transport materials, and predicted date in which a patient expects to receive a final manufactured drug for infusion all depend upon the capacity of a manufacturing facility to manufacture the therapeutic drug. As such, there are challenges with communicating scheduling information and capacity information. Given the rise of personalized medicine supply chains and the existence of several challenges associated with such supply chains, there is a need for new technologies to solve these problems.

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later. In one or more embodiments, described herein are systems, devices, apparatuses, computer program products and/or computer-implemented methods that facilitate an interaction between an individualized medicine system and one or more nodes of a blockchain configured to store event data and identification data corresponding to transactions that occur along an individualized medicine supply chain.

According to an embodiment, a computer-implemented method is provided. In an aspect, the method can include accessing, by a user device, an individualized medicine system operatively coupled to a processor. In another aspect, the computer-implemented method can comprise transmitting, by the user device, a query request to the individualized analytics system to perform a chain of identity analysis or chain of custody analysis. The computer-implemented method can also comprise receiving, from the individualized analytics system, chain of identity data or chain of custody data. In yet another aspect, the computer-implemented method can comprise outputting, by a user interface of the user device, the chain of identity data or the chain of custody data, wherein a display module of the user interface is effective to: render at least one of text data, video data, image data, or audio data associated with the chain of identity data or the chain of custody data.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section. One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Techniques described herein provide cloud-based platform technologies that allow for the execution of a range of operations related to transactions that occur as part of an individualized medicine supply chain. Various implementations receive data from multiple data sources, identify attributes of the data, and execute an operation to facilitate a stakeholder activity in connection with the personalized medicine supply chain. For instance, in a non-limiting aspect, techniques described herein provide for the coordination of supply chain events (e.g., automated courier scheduling, raw material delivery, kit tracking capabilities, raw and final product preparation, streamlining ordering and scheduling, capacity and resource management, and several other activities). Furthermore, systems, devices, methods, environmental and architectural embodiments disclosed herein disclose one or more platform technology that facilitates a multi-tenant deployment of managing platform identity information, facilitating regional separation capabilities to support data residency requirements of the system, and/or facilitates satisfying separation requirements between controlled data set users and uncontrolled data set users. In an aspect, an example environment is disclosed in which various aspects described herein can be employed.

Figure 1A:
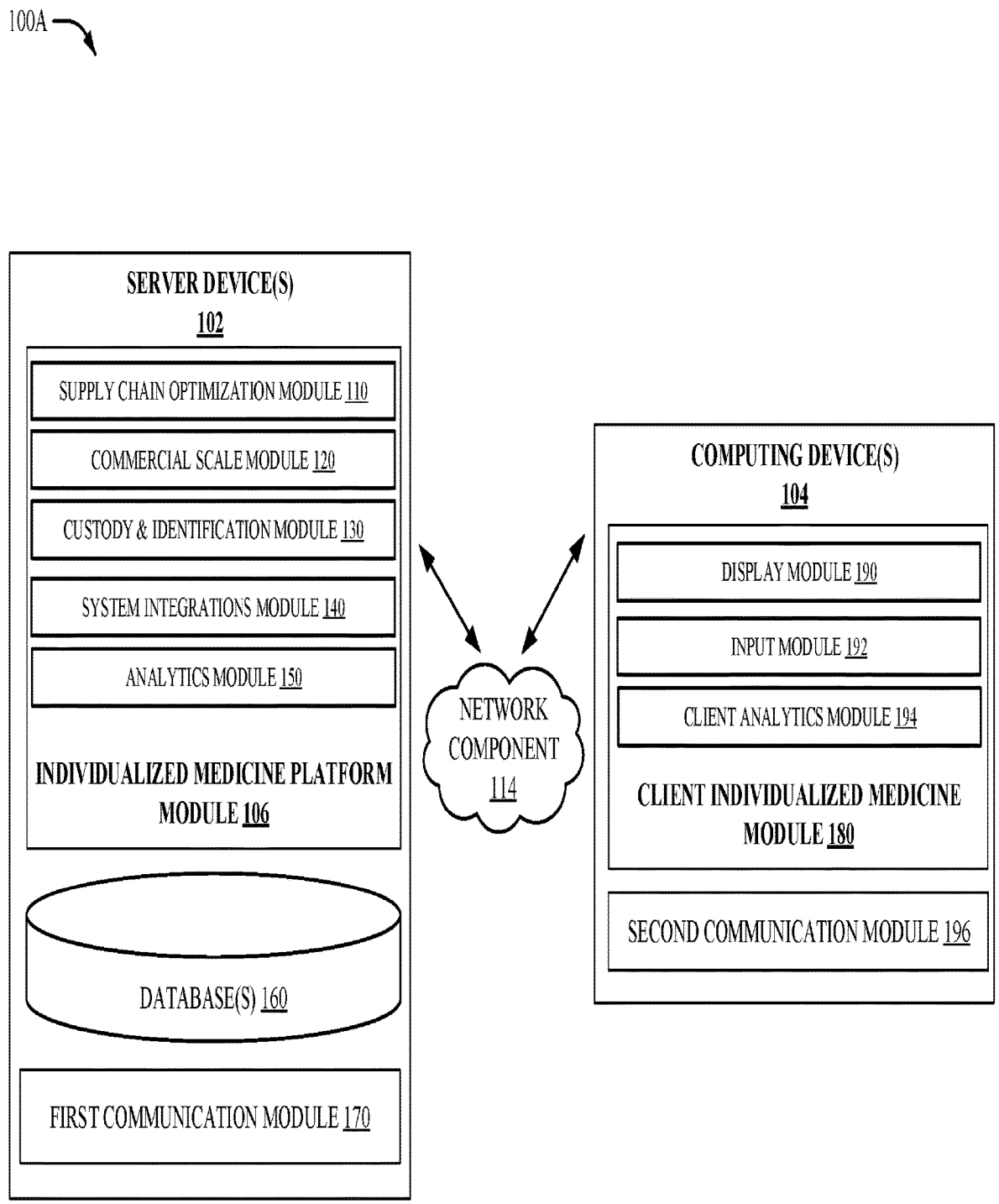
FIG. 1A illustrates an example, non-limiting block diagram of a representative environment 100A in which event data and activity data associated with a personalized medicine supply chain can be generated and stored in accordance with one or more embodiments described herein.

FIG. 1A illustrates an example, non-limiting block diagram of representative environment 100A in which an example system can be used to generate, analyze, identify, track, and store event data, activity data, identifier data, and other such data items associated with a personalized medicine supply chain in accordance with one or more embodiments described herein. In an aspect, environment 100A can include one or more server device(s) 102 and one or more computing device(s) 104 that can generate, curate, track, monitor and store data associated with transactional processes of an individualized medicine supply chain. For instance, environment 100A can facilitate a tracking of events associated with manufacturing gene therapies and cell therapies for target patients. In an aspect, computing device(s) 104 can be a desktop computing device, smart phone, tablet, laptop, smart watch, and other suitable type of computing device.

In an aspect, the terminology "individualized medicine supply chain" or "personalized medicine supply chain" and other variations are used to denote information that is generated from a combination of activities, events, materials, and devices utilized by various stakeholders to procure a personalized medicine therapeutic for a patient. In an aspect, an individualized medicine supply chain can begin with a decision to treat a patient with a personalized therapy (e.g., a therapeutic medicine manufactured from a patient's own biological materials such as cells) to the manufacturing of a personalized therapeutic medicine and finally to a point of infusing the personalized therapeutic medicine into a patient vein. For example, server device(s) 102 can acquire data, process the data to curate the acquired data, and generate queries for application to the data to perform various analytics, generate reports, track a chain of identity of various materials, track a chain of custody associated with various materials, and execute other such operations. In another aspect, server device(s) 102 can include individualized medicine platform module 106 that can employ various operations in connection with supply chain optimization module 110, commercial scale module 120, custody & identification module 130, system integrations module 140, analytics module 150, and other such modules.

In an aspect, individualized medicine platform module 106 can perform a range of operations related to data corresponding to individualized supply chain events such as point-of-care collection (e.g., collection of samples that meet threshold quality standard requirements), tracking supply chain events (e.g., as relates to manufacturing a personalized therapeutic for a patient), optimizing resources (e.g., fulfilling manufacturing orders), security and compliance (e.g., ensuring data quality, data validation, and data encryption mechanisms are implemented), supply chain orchestration events (e.g., scheduling couriers, raw material delivery, tracking kits and materials and raw materials), ordering and scheduling activities (e.g., scheduling of sample collections, manufacturing, administration of medicine, etc.), reporting tasks (e.g., reporting quality findings, compliance activities, chain of identity information, chain of custody information, etc.), and/or facilitating system integrations (e.g., data integrations, data modifications, insight procurement, etc.).

In an aspect, individualized medicine platform can employ supply chain optimization module 110, commercial scale module 120, custody & identification module 130, system integrations module 140, and analytics module 150 to perform a range of operations (e.g., by providing instructions for execution by a processor of server device(s) 102).

In an aspect, individualized medicine platform module 106 can employ supply chain optimization module 110 to execute ordering operations, scheduling operations, and resource planning operations. Furthermore, supply chain optimization module 110 can execute tasks that orchestrate logistical events (e.g., coordinate couriers) and perform data (e.g., representing the movement of materials and/or products through the individualized medicine supply chain) tracking tasks to allow for transparent visibility of activities performed along the individualized medicine supply chain. For instance, supply chain optimization module 110 can execute scheduling operations corresponding to pickup and delivery of raw materials, final products, biological materials, and other such items by stakeholders (e.g., couriers, third party logistics providers, etc.) to create efficiencies in transportation of materials.

In an aspect, individualized medicine platform module 106 can execute supply chain optimization module 110 to facilitate ordering one or more therapy for a patient. For instance, supply chain optimization module 110 can intake one or more indication data sets, therapy descriptive data sets, patient information (e.g., name, date of birth), study detail data (e.g., if a patient is affiliated with a study), patient consent data, order cancellation data, and other such information. Furthermore, supply chain optimization module 110 can facilitate a selection of a treatment ordering site (e.g., center of excellence) and treatment prescriber (e.g., physician data). In a non-limiting embodiment, supply chain optimization module 110 can employ a set of rules and requirements to limit selection options based on intake data as applied against a set of ordering rules customized to a particular set of circumstances (e.g., patient conditions, capacity conditions, delivery conditions, etc.).

In another aspect, supply chain optimization module 110 can execute scheduling operations. For instance, supply chain optimization module 110 can intake data corresponding to scheduling a therapeutic order such as collection site data, contact data, delivery site data, calendar scheduling data, and other such data. In a non-limiting embodiment, supply chain optimization module 110 can employ a set of rules and requirements applied against intake data to determine a limited selection of options allowable for scheduling. For instance, one or more rules can correspond to existing courier scheduling dates, therapy-specific conditions for transportation and delivery time constraints, logistical restrictions, and other such requirements.

In an aspect, machine learning techniques can be employed to group such intake data and evaluate data patterns related to ordering and scheduling. Furthermore, in some non-limiting embodiments, machine learning operations can be employed to determine predictive likelihoods and/or predictive efficiencies to be achieved from selecting a combination of ordering and selection related to a therapy, region, user, and other such platform attributes. In another aspect, various constraints, requirements, and rules can applied against intake data by supply chain optimization module 110 in order to effectuate occurrence of timely ordering and scheduling events. For instance, once collected, patient blood has shelf-lives and expiration dates after which the material is no longer usable to manufacture therapeutic products. Accordingly, individualized medicine platform module 106 employs rules and conditions to ensure the material has an efficacious transition through the supply chain up through infusion as a finished therapeutic product into a patient.

In another aspect, supply chain optimization module 110 can execute (e.g., using a processor) product tracking operations to facilitate transparency as supply chain events occur. For instance, supply chain optimization module 110 can acquire, curate, analyze, integrate, and/or generate data associated with a material workflow through various stages of a supply chain. As a non-limiting example, supply chain optimization module 110 can receive scheduling data (e.g., representing instructions to execute a scheduling task) from client individualized medicine module 180 (e.g., receiving data from input module 192), where the scheduling data represents the event of collecting blood samples from a center of excellence (e.g., hospital qualified for a respective therapy). Furthermore, supply chain optimization module 110 can receive data (e.g., from a sensor incorporated into the kit, from courier data confirming delivery of the kit, from a smart label attached to the kit, etc.) associated with the delivery of a kit to the center of excellence to facilitate the extraction of the blood samples (e.g., at a point of care setting) and submission of such sample within a kit. In another aspect, supply chain optimization module 110 can receive collection data representing a confirmation that the kit with the blood sample has been picked up by a courier. In an aspect, supply chain optimization module 110 can further receive data indicating cells (within the blood) have been shipped (in the process of being transported) to a manufacturing facility.

In a non-limiting embodiment, supply chain optimization module 110 can execute collection (e.g., blood collection) operations. For instance, supply chain optimization module 100 can intake data corresponding to scheduling a collection of blood such as patient (blood) test result data, patient collection bag label data, patient identity data, collection bag identification data (e.g., unique donation number, apheresis ID, site data, etc.), patient data (e.g., weight data, CBC count), bag detail data (e.g., amount of blood collected (mL), anticoagulant type, anticoagulant volume, collection start time/end time, change of custody confirmation data (e.g., bag identifier label or scanned bag data), collection bag shipping data, and other such data. In a non-limiting embodiment, supply chain optimization module 110 can employ a set of rules and requirements to limit selection options based on intake data as applied against a set of collection rules customized to a particular set of circumstances (e.g., patient conditions, capacity conditions, delivery conditions, collection facility scheduling constraints, etc.).

In other aspects, supply chain optimization module 110 can generate and/or receive tracking data associated with events along the manufacturing portion of the supply chain (e.g., track and confirm that a courier shipment has been received, quality inspection occurred and results are compared to a threshold target result, manufacturing of personalized therapeutic has commenced, quality inspection occurred and results were compared to a threshold target result, finished product has shipped, etc.) and the patient administration portion of the supply chain (e.g., tracking of therapeutic until receipt by center of excellence, scheduling of infusion of therapeutic, infusion occurred, long-term tracking of patient outcome, etc.).

In a non-limiting embodiment, supply chain optimization module 110 can execute satellite manufacturing (e.g., personalized therapies) operations. For instance, supply chain optimization module 100 can intake data corresponding to scheduling a satellite manufacturing operation. For instance, supply chain optimization module 110 can intake data such as therapy data, study number data (if applicable), Chain of Identity (COI) information, shipment verification data, collection data, receiving documentation data (e.g., is the raw material kit shipped properly such as inside a specialized pouch, was the raw material stored at required temperatures such as temperatures to preserve a vapor phase of liquid nitrogen as per some material requirements, missing items, mismatching numbers, damages, etc.), shipment verification data, number of (blood) bag data, print label data, confirmation data (e.g., manufacturer labels applied to bags), COI identifier scan data on collection bag and/or cassette (if applicable), cryopreservation data (e.g., product volume data, mononuclear cell count data, cell viability data, summary data, bag shipment data, quality release data, document release data, transfer data, authorized user signature data, shipping checklist data, and other such data. In a non-limiting embodiment, supply chain optimization module 110 can employ a set of rules and requirements to limit selection options based on intake data as applied against a set of satellite manufacturing rules customized to a particular set of circumstances (e.g., patient conditions, capacity constraints, delivery conditions, manufacturer facility scheduling constraints, etc.).

In another non-limiting embodiment, supply chain optimization module 110 can execute central manufacturing (e.g., personalized therapies) operations. For instance, supply chain optimization module 100 can intake data corresponding to scheduling a central manufacturing operation. For instance, supply chain optimization module 110 can intake data such as lot number data (e.g., manufacturing lot number for the therapeutic product), confirmation data, shipment condition data, shipment detail data, shipment COI identification data, air waybill data, shipment pouch data, first stimulation data (e.g., start date data), second stimulation data, harvesting data (e.g., start date data), final product data (e.g., number of bags of therapeutic after manufacturing process, product expiry date data, product label data (e.g., print ready label for bag of final product), label attachment confirmation data, respective bag number label application data, unused label disposal data, bag selection data (e.g., for shipment), quality release data, product transfer to shipper data, shipping checklist data, and other such intake data.

In a non-limiting embodiment, supply chain optimization module 110 can employ a set of rules and requirements to limit selection options based on intake data as applied against a set of central manufacturing rules customized to a particular set of circumstances (e.g., patient conditions, capacity constraints, delivery conditions, manufacturer facility scheduling constraints, etc.). In an aspect, supply chain optimization module 110 can provide scheduling options based on manufacturing capacity data. For instance, a set of scheduling date options can be provided for scheduling manufacturing based on manufacturing capacity data queried by supply chain optimization module 110.

As such, various system components such as the scheduler component and manufacturing capacity component can be used to satisfy requirement criteria to facilitate a system determination (e.g., date availabilities for manufacturing occur). In another instance, a capacity-based scheduling operations employed by supply chain optimization module 110 can utilize scheduling rules that correspond to a number of manufacturing slots available per week, number of slots currently scheduled, additional bookings available for the week, and generate determinations (e.g., using supply chain optimization module 110) as to dates and times available for manufacturing. Furthermore, capacity-based scheduling operations can include supply chain constraints and rules such as number of manufacturing legs required, number of shipping legs required for product to arrive, time for shipment, and other such considerations.

In an aspect, scheduler component and manufacturing capacity component can provide a normalized view of manufacturing capacity across distributed manufacturing sites (e.g., sites owned by pharma companies, independent contract manufacturing organization (CMO) sites). Furthermore, manufacturing capacity component can access data from multiple data stores to allow scheduler component to provide a unified view of manufacturing capacity by region, site, or other segment to ascertain capacity capabilities and constraints. Furthermore, in a non-limiting embodiment, manufacturing site capacity data can be stored in a registry at server device(s) 102 (e.g., database(s) 160) in order to accommodate data from a variety of manufacturing site sources (e.g., data sourced via integrations such as Manufacturing Execution Systems (MES) systems).

In an example non-limiting instance, a healthcare provider (HCP) responsible for administering particular therapies can execute an order for a therapy (e.g., therapy permitted to order) associated with a customer instance at individualized medicine platform module 106. Furthermore, scheduling component can determine capacity data from distributed center of excellence capacity registry data store that comprises distributed apheresis site capacity data and infusion site capacity data (e.g., unreserved capacity and contractually reserved capacity for therapies). Furthermore, scheduler component can employ manufacturing capacity component to access data from customer specific capacity registries associated with distributed manufacturing sites published capacity data to determine manufacturing site capacity capabilities. As such, manufacturing capacity data can be based on customer configuration information and scheduling rule requirements. Furthermore, scheduling component can employ predictive determination components that predict manufacturing times (e.g., based on machine learning analysis of historical and current data), optimize scheduling activities, and determine waitlist and over-scheduling decisions based on site specific rescheduling data and rules.

In other aspects, supply chain optimization module 110 can also execute operations based on intake of distribution center (e.g., global distribution) intake data (e.g., specimen status upon receipt, shipment verification data, COI data, condition of shipment data, etc.) and order status tracking intake data or presentation data (e.g., shipping status, satellite lab status, manufacturing status, distribution center status, infusion status, etc.). For instance, the collection stage can be presented (e.g., using display module 190) at a user interface with stage data, phase data (e.g., test result stage), shipping stage data (e.g., pending, shipped, complete, etc.), site data (e.g., center of excellence, cryogenic laboratory, test institution, distribution center, hospital, etc.), timeline data, and other such information.

In yet another aspect, supply chain optimization module 110 can also execute operations such as cancellation of approved orders (e.g., intake order cancellation request data, etc.), cancellation of in-progress or submitted orders (e.g., patient consent data, order cancellation request data, etc.), rescheduling of tasks (e.g., collection, manufacturing, infusion, etc.), intake of infusion intake data (e.g., product and/or shipment receipt data, transfer product to storage data, condition of shipment data, real-time tracking data, real-time alert notification data, etc.), user management operations (e.g., creation of a user, etc.), change request operations, and other such operations. In an aspect, each operation requires authentication of one or more user and each operation can be performed by different authorized users and user devices corresponding to predefined permissions.

For instance, a first user (e.g., nurse, staff member) at a first site (e.g., center of excellence, hospital, etc.) may be assigned permissions to enroll patients and place orders for a patient therapy, a second user (e.g., patient operations or central scheduler user) at a second site (e.g., manufacturing facility) may be assigned permissions to access enrollment documentation (e.g., via individualized medicine platform module 106) and initiate transmission of a therapeutic order to a third user (e.g., logistics personnel) at a second site (e.g., manufacturing facility) with permissions to approve a therapy order and schedule a shipment of the therapy. Furthermore, the second user may be assigned permissions to send product data to first user. In such instance, each user device is assigned roles having permissions and limitations to facilitate execution of respective operations using individualized medicine platform module 106.

In an aspect, computing device 104 can employ display module 190 to transform the data to various types of output information (e.g., text, charts, video, audio, graphs, tables, and other such output) that are based upon order data, schedule data, capacity data, patient identification data, sample identification data, courier data, manufacturer data (e.g., batch number), electronic record data, milestone data associated with medicine manufacturing, medicine quality data (e.g., cell count data), notification data, storage data (e.g., cryogenic storage of sample), patient treatment data, patient outcome data (e.g., long-term monitoring), payment data (e.g., reimbursement information), assay quality control data, sample storage data (e.g., temperature data of a storage facility received from temperature sensors, orientation or tilt data of a package containing patient samples or therapeutic medicines, humidity data of a manufacturing environment, etc.), monitoring data (e.g., information corresponding to sensors such as GPS sensors employed in factories, warehouses, laboratories, pharmacies, etc.), financial data, inventory data, and other such data.

In another aspect, supply chain optimization module 110 can generate, receive, curate, and/or transform ordering data, scheduling data, and/or resource management data. In an aspect, ordering data can represent instructions to order raw materials, patient samples, intermediary materials, final products (e.g., therapeutic drugs), and other such items associated with the individualized medicine supply chain. In an aspect, several stakeholders (e.g., manufacturers, physicians, patients, etc.) can execute ordering tasks based on authorization data representing permission credentials to perform an order. Furthermore, in an aspect, supply chain optimization module 110 can generate, receive, curate, and/or transform scheduling data to facilitate a coordination of collection (e.g., by nurses, couriers, manufacturers, etc.), manufacturing, and treatment administration of materials and final products. As such, supply chain optimization module 110 can facilitate the streamlining of scheduling and coordination activities. In yet another aspect, supply chain optimization module 110 can perform resource management tasks to optimize manufacturing capacities to manufacturing needs of patient and efficiently coordinate the fulfillment of orders for final products, raw materials, and/or samples.

In another non-limiting embodiment, individualized medicine platform module 106 can employ commercial scale module 120 (for execution by a processor of server device(s) 102) to perform operations such as acquiring and curating data associated with the manufacturing of personalized medicines, training of various stakeholders (e.g., onboarding, training and collaboration activities of healthcare providers), and configuration tasks (e.g., configuring modules and functions of the platform to perform client specific activities such as clinical activities, etc.). For instance, commercial scale module 120 can perform operations and functions to facilitate a determination as to whether manufacturing events or activities comply with manufacturing and compliance standards starting with point of care activities through manufacturing and final product delivery activities. As a non-limiting example, commercial scale module 120 can execute operations to ensure that a patient's identity is confirmed and verified (e.g., compare driver's license data, signature data, etc.), that labels are verified to contain correct information, and correct products have been shipped.

In another aspect, commercial scale module 120 can perform operations associated with payment reimbursement for the performance of activities associated with individualized therapies. For instance, commercial scale module 120 can acquire, generate, and curate data associated with triggering events related to the procurement and administration of individualized therapies for patients. In an aspect, such triggering events can correspond to requirements that satisfy payer data needs (e.g., for payment reimbursement to occur) and commercial operator data needs. In another aspect, commercial scale module 120 can receive payment data and transform such payment data in various formats and structures that can expedite automated payment mechanisms that satisfy payment process requirements (e.g., revenue recognition processes). Furthermore, in an aspect, commercial scale module 120 can monitor patient data and transform patient data over a long-term period of time.

In another non-limiting embodiment, individualized medicine platform module 106 can employ custody & identification module 130 (for execution by a processor of server device(s) 102) to perform operations such as acquiring, generating, curating, transforming, monitoring, and storing data associated with chain of identity and/or the chain of custody of various entities, materials, and product along the individualized medicine supply chain. For instance, custody & identification module 130 can perform operations (e.g., such as generating and storing location data associated with a sample) that can allow for the traceability of patient samples (e.g., blood, cells, etc.).

As a non-limiting example, chain of custody & identification module 130 can perform audit operations (e.g., curate data and generate data representing an audit trail of handling events of cell products, custodial events associated with any product or material, identification correspondence of any material or product, etc.), quality validation operations (e.g., perform data quality validation checks and process validation reviews of data), record generation operations (e.g., create a platform of record of all data to enable transparency and instill confidence in stakeholders, generate reports based on data, etc.), and perform security operations such as encrypting data and performing authorization and validation operations to ensure only authorized user profiles can access respective data sets and representative information. In an aspect, chain of custody & identification module 130 can acquire and curate a set of data that includes time data that an event occurred, event identifier (e.g., signature occurred, label scanned, etc.), signature data associated with the identity of an entity performing a task at such time, description data describing the event that occurred (e.g., verification of a patient, scanning a label, ensuring a label matched an identifier number, verifying apheresis occurred, handing off a raw material to another entity, etc.), location data, identity data of a user profile performing the event.

In an instance, a chain of custody (COC) event ca be tracked via a scanning of a label corresponding to a raw material (e.g., blood) from the time it leaves a patient body (e.g., collection), through its path throughout the supply chain (e.g., shipment, cryogenic storage, manufacturing, etc.) to infusion of the therapeutic (e.g., blood) into the patient body. In an aspect, custody & identification module 130 can intake chain of custody and chain of identity (COI) data from a label (e.g., on a blood bag) via a scanning mechanism or other intake form. As an example, a chain of custody event can occur upon a raw material arriving at a manufacturing facility and custody & identification module 130 can intake such COC events. In another instance, a raw material arriving at a cellular laboratory can present several COC events taken in by custody & identification module 130.

At day 1, cell processing data can be utilized by supply chain optimization module 110 and corresponding COI event data (based on a scanning of the blood bag label) can be generated by custody & identification module 130. Furthermore, upon the bag being labeled and readied for shipping, upon another scanning of the label, a COC event can be generated by custody & identification module 130. Likewise, a COI and COC event can be generated by custody & identification module 130 based upon an occurrence of a shipping event (e.g., location to location material transition), a manufacturing quality user evaluating the test results of a manufactured product, a manufacturing operator confirming an occurrence of COC event (e.g., person to person material transition), and other such events. In an aspect, custody & identification module 130 can generate a data store of all login events capable of access via one or more query request initiated using client analytics module 194. Furthermore, custody & identification module 130 can generate a COI transaction log corresponding to all events coupled to a COI number. Also, custody & identification module 130 can generate a COC transaction log representing each occurrence of a hand-off of raw material and/or product throughout the supply chain.

In another non-limiting embodiment, individualized medicine platform module 106 can employ system integrations module 140 (for execution by a processor of server device(s) 102) to integrate data from other systems with data generated, acquired, curated, analyzed and stored within database 160 or other data stores of environment 100A. In an aspect, system integrations module 140 can perform system integration operations such as acquiring, curating and storing data extracted from courier systems, enterprise resource planning systems, customer relationship management systems, manufacturing execution systems (MES), laboratory information management systems (LIMS), electronic batch record system (EBR), and quality management system (QMS). In general, individualized medicine platform 106 can facilitate the coordination, orchestration, and performance of ordering and scheduling operations, collection operations (e.g., acquiring data as per GMP requirements), transportation operations (e.g., generating data related to logistics activities, creating efficiencies via logistics automation), manufacturing operations (e.g., managing and controlling the deployment of resources), delivery operations (e.g., generate product tracking data), and payment reimbursement operations (e.g., acquiring and evaluating data related to administration of therapeutic).

In a non-limiting embodiment, systems integration module 140 can integrate systems that perform operations in connection with individualized medicine platform module 106 operations via various integration mechanisms. As an example, an onboarding subsystem that executes patient and site (e.g., center of excellence, hospital, etc.) onboarding operations (e.g., hub and patient support systems) can integrate with supply chain optimization module 110 to facilitate center of excellence setup tasks and patient selection activities. Furthermore, integration module 140 can integrate supply chain optimization module 110 with an electronic health record (EHR) system or LIMS system to facilitate individualized medicine platform module 106 execute patient scheduling operations in connection with cell and tissue collection tasks and constraints accessed from the HER and/or LIMS systems.

As another example, integration module 140 can integrate supply chain optimization module 110 and logistics systems to facilitate execution of scheduling, tracking, monitoring, and other logistics operations by individualized medicine platform module 106 based on shipping constraints (e.g., bookings, weather delays, etc.) provided by logistics systems. Accordingly, other integrations facilitated by integration module 140 can include individualized medicine platform module 106 integrating the individualized medicine platform module 106 manufacturing scheduling capabilities (e.g., scheduling he manufacturing slots) with enterprise resource planning (ERP) systems (e.g., manufacturer ERP's indicating manufacturing capacity constraint information), Chain of Identity (COI) and/or Chan of Custody (COC) recordation operations with IVIES systems (e.g., based on manufacturing traceability information), infusion operations with HER and/or Hub systems (e.g., indicating product delivery information and constraints upon which infusion is based), payer reimbursement operations with reimbursement hub systems (e.g., indicating order-to-cash data), and/or ongoing monitoring operations with Real World Evidence Systems (RWE) (e.g., to provide access to data regarding usage, benefits and risks of the therapy).

In another aspect, integration module 140 can employ a unified authentication system to execute authentication of an identity of a user (e.g., identity provider) utilizing individualized medicine platform module 106 and integrated systems (e.g., using integration module 140) such as a web application, a web service system, a storage service (e.g., data store, database, server, etc.) employed to perform a task in connection with the individualized medicine platform module 106. In an instance, an access management system or identity provider (e.g., employed across one or more server) can be configured to integrate (e.g., using integration module 14) with individualized platform module 106 and other systems in accordance with user (e.g., customer such as pharmaceutical company) criteria to act as an identity authentication mechanism to authenticate user identity and respective user roles (e.g., user permissions to execute a limited set of operations). In an aspect, the access management system can execute operations such as creation, maintenance and management of identity information of users and authentication operations for individualized medicine platform module 106 and integrated systems based on storage of user credential data.

In an aspect, an access management system in connection with integration module 140 can employ a single sign on (SSO) authentication mechanism configured to relate a user identity (e.g., user device identity) used to access multiple integrated system service providers and the individualized medicine platform module 106. As such, the access management system can be configured to execute authentication operations in a shared manner across one or more service provider applications and/or devices (e.g., using an SSO protocol and trust relationship mechanisms). In an aspect, individualized medicine platform module 106 can store (e.g., in one or more instance database employed across one or more server devices) profile metadata representing one or more user profile (E.g., name data, unique identifier data, address data, picture data, etc.).

In an aspect, user profile data can be stored across multiple instance databases, however, access management system can allow for a single login (e.g., authentication mechanism and provider) to be shared across different instance databases. Furthermore, in an aspect, access management system can store user credential metadata (e.g., login ID, password, etc.) representing authentication information in one or more credential data store (only associated with access management system) of the access management system. In an aspect, the credential data store can store user credential data for all users (across all integrated systems and platforms) as well as groups of users. As such, access management system can execute authentication operations across all users (e.g., pharmaceutical client users, website users, customer support users, etc.). In a non-limiting embodiment, a user can refer to a device accessing (e.g., via login) the individualized medicine platform module 106 as a representative of an institute to execute various operations within a step of the individualized medicine supply chain for a therapy in a respective region. Furthermore, a user can be a member of a group in an identity provider (e.g., pharmaceutical company, hospital, infusion center, manufacturing facility, etc.) where such membership is mapped to a role (e.g., role 1 can access personal health identifier (PHI) information for therapy A, role 2 is restricted from accessing PHI for therapy A) within such identity provider corresponding to respective permissions (e.g., executable actions or operations permitted by user) on a therapy in a region.

In an aspect, an identity provider (IDP) can refer to an entity configured to create, maintain, and manage identity information for user profiles and devices of individualized medicine platform module 106 while providing authentication services to integrated applications (e.g., within a federated or distributed framework in various non-limiting embodiments). In an aspect, an IDP is configured to provide a verification source of user credentials for individualized medicine platform module 106 and integrated applications. As such, an IDP can provide a trust relationship (and in some instances a single-sign on protocol to facilitate execution of authentication operations for individualized medicine platform module 140 and any number of respective integrated components (e.g., using integration module 140). In an aspect, integration module 140 can enable an assignment of permissions to a range of users. Accordingly, a user device need only access the platform module 106 to access authentication activities for any number of platform subsystems.

For instance, a system administrator user can have escalated permissions to change administrator identities or add administrators. In another instance, integration module 140 can assign an identity administrator (also referred to as an onboarder) permissions to add, change or remove other users from the platform, and assign or revoke permissions and roles to/from other users, however, the identity administrator may not remove system administrators in some embodiments. In yet another aspect, integration module 140 can assign an end user roles and permissions to execute day to day operational tasks via the individualized medicine platform module 106.

In yet another non-limiting embodiment, individualized medicine platform module 106 can also employ analytics module 150 that can acquire data (e.g., data associated with individualized medicine platform 106), curate the acquired data, generate queries for various types of analytics, determine data to include in a response to such queries, and generate output information responsive to the generated queries. In an aspect, analytics module 150 can employ machine-learning algorithms and/or models to extract data from curated data sets in response to multiple generated queries performed by analytics module 150. In an aspect, the data extracted using the queries can be utilized to identify various insights based on the application of machine-learning algorithms and/or models. In another aspect, the insights can be integrated and transformed into other insights.

Furthermore, in an aspect, the insights can be used to generate analytics output information (e.g., charts, graphs, video, audio, etc.). As an example, machine learning algorithms can be applied to historical data to perform predictive analysis of whether sufficient material supplies (e.g., vectors) and other resources are available to manufacture a final product therapeutic. Furthermore, in another aspect, real world evidence data (e.g., longitudinal patient experience data, treatment data, outcome data, clinical data, genomic data, other data generated from patient experiences outside of clinical trials) can be utilized to inform leanings of machine learning algorithms (e.g., adjust model parameters or hyper parameters) to facilitate the execution of more effective predictions, define a efficacy of a model, extract learnings from data, adjusting predictive modeling problems, and other such utility. Furthermore, in another aspect, real world data can be utilized as a feedback loop mechanism to make data quality assessments, adjust analytical models or tweak the mechanism by which modules execute various operations or tasks.

In an aspect, the term module is used to denote any combination of software, hardware and/or firmware that can be configured to provide the corresponding functionality such that individualized medicine platform module 106 and client individualized medicine module 180 can be implemented using any of these combinations. In various implementations, individualized medicine platform module 106 can correspond to a client application that renders a user interface (e.g., using display module 190) on a corresponding display device of computing device 104, and communicates over a network to a server application, such as individualized medicine platform module 106. Alternatively, or additionally, client individualized medicine module 180 can represent a stand-alone application that includes the functionality of individualized medicine platform module 106 onto a same device. In one or more implementations, server(s) device 102 can represent one or more server that distribute various aspects of the individualized medicine platform module 106 across the multiple devices and/or provide cloud-based services to multiple user devices.

In another aspect, server device(s) 102 can comprise first communication module 170 configured to communicate with external devices and can represent a combination of hardware, software, and/or firmware that are configurable to facilitate the exchange of information, such as images, addresses, audio, video, commands, queries, messaging, generation of analytics and other such information. In another aspect, first communication module 170 can include one or more protocol stacks associated with a network over which data is exchanged, firmware that drives hardware to generate signals and/or process messages used in maintaining a wireless and/or wired communication session, etc. In some implementations, first communication module 170 can include computer networking ports, such as a Transmission Control Protocol (TCP) port, a User Datagram Protocol (UDP) port, a File Transfer Protocol (FTP) port, a Hypertext Transfer Protocol (HTTP) port, an Internet Message Access Protocol (IMAP) port, and so forth. Various implementations of first communication module 120 can include physical communication ports, such as a serial port, a parallel port, a Universal Serial Bus (USB) port, a keyboard port, a display port, an audio port, etc. In various implementations, server device(s) 102 can use first communication module 120 to connect with other devices over network component 114, such as computing device(s) 104.

In an aspect, network component 122 can represent any suitable type of communication network that facilitates a bi-directional link between various computing devices. Furthermore, network component 122 can include communication networks interconnected comprising elements such as a WLAN, ethernet access, wireless telecommunication network interconnected with the internet, Wi-Fi access point connected to the Internet, an IOT network, and other such networks. In another aspect, computing device(s) 104 can include client analytics module 194 that represents user profile access to some or all of the functionality provided by analytics module 150. In another aspect client analytics module 194 can represent a browser that remotely logs onto a website hosted by server device(s) 102. Further, while client analytics module 194 and analytics module 150 are illustrated as residing on separate devices, some implementations combine some or all the respective module functionality into a single computing device as further described herein.

In various implementations, computing device(s) 104 can use client analytics module 194 to access cloud-based services provided by server device(s) 102 to obtain individualized medicine data, insights generated from the data, and other information (e.g., key performance indicators) further described herein. In another aspect, client individualized medicine module 180 can includes input module 192 to provide user access into features provided by analytics module 150 such as inputting a search query, inputting user feedback, requesting reports, accessing a dashboard and/or corresponding reports, scheduling data curation, scheduling data analysis, ordering data curation, ordering data analysis, transportation data curation, transportation data analysis, scoring vendor performance, adding databases for data curation, and so forth. In another aspect, computing device(s) 104 can include second communication module 196 to facilitate communications over network component 114. As one, example, computing device 104 can use second communication module 196 go communicate with individualized medicine platform module 106. Furthermore, in an aspect, second communication module 196 can represent any suitable combination of hardware, software, and/or firmware that is configurable to facilitate data exchanges with other devices.

In a non-limiting embodiment, individualized medicine platform module 106 can comprise supply chain optimization module 110, commercial scale module 120, custody & identification module 130, system integrations module 140, and analytics module 150 to work in concert to provide medicine supply chain monitoring, tracking, scheduling, ordering, analytics, querying, and other interactive features. Some combinations of these modules communicate with one another to exchange information, such as by defining data structures according to a set of rules to provide a mechanism for cross-entity data sharing, as well as predictable and repeatable processing by different entities to achieve expected results. For example, the set of rules can outline the type of information the supply chain data included in the data structure describes, an amount of supply chain data stored within the data structure, a format in which the supply chain data is stored within the data structure, and other such information types.

By following these rules, a first entity can create and store a data structure such that a second entity can successfully access and interpret the data included in the data structure. A data structure can include any suitable type of structure in which data can be stored, defined, and/or retrieved, such as an object, a vector, a table, a tree, a graph, a queue, a linked-list, a record, a union, a set, a string, a list, an array, a container, a matrix, a function parameter, a heap, and other such structures. In an aspect, server device 102 can include an ordering module 110 that acquires, processes and curates data associated with ordering activities in a personalized medicine supply chain. For example, the supply chain can include the acquisition and generation of order data associated with ordering a courier to pick up or drop off a collection sample. In another aspect, server device 102 can include an ordering module 110 that acquires, process and curates data associated with ordering activities in a personalized medicine supply chain. For example, the supply chain can include the acquisition and generation of order data associated with ordering a courier to pick up or drop off a collection sample.

In an aspect, a patient's blood sample with cells may be collected at a center of excellence (e.g., hospital) and transported to a manufacturing facility to manufacture the personalized therapeutic medicine and the personalized therapeutic medicine must again be transported back to a COE for infusion into a patient. In an aspect, supply chain optimization module 110 can acquire order data representing a wide range of ordering information such as shipment destination, shipment origin, storage conditions during transport, required temperature conditions during transport, handling instructions, instructions to place an order with a particular carrier, type of transportation mode (e.g., ground transport, air transport, etc.), sample information (e.g., quantity, type of sample, etc.).

Furthermore, in an aspect, custody & identification module 130 can acquire, generate, curate, store, and query chain of identity information (e.g., patient identification information corresponding to a sample, patient identification information corresponding to a personalized medicine, medicine specifications, courier identification information, manufacturer identification information, storage facility identification information, supplier identification information of raw material, etc.), chain of custody information (e.g., temperature data, tilt data of package, tracking a sample or medicine custodian at a given point in supply chain, etc.), and other such ordering information. In an aspect, this non-limiting example of an ordering feature of individualized medicine platform module 106 illustrates how any suitable type of order data can be acquired, generated and/or stored by ordering module 110 and how modules can perform operations in combination with other modules. In an aspect, server(s) device 102 can include database device(s) 160 to represent any suitable source of data and/or information. Alternatively, or additionally, database device(s) 160 can represent storage for data generated by the medicine supply chain module 106.

Figure 1B:
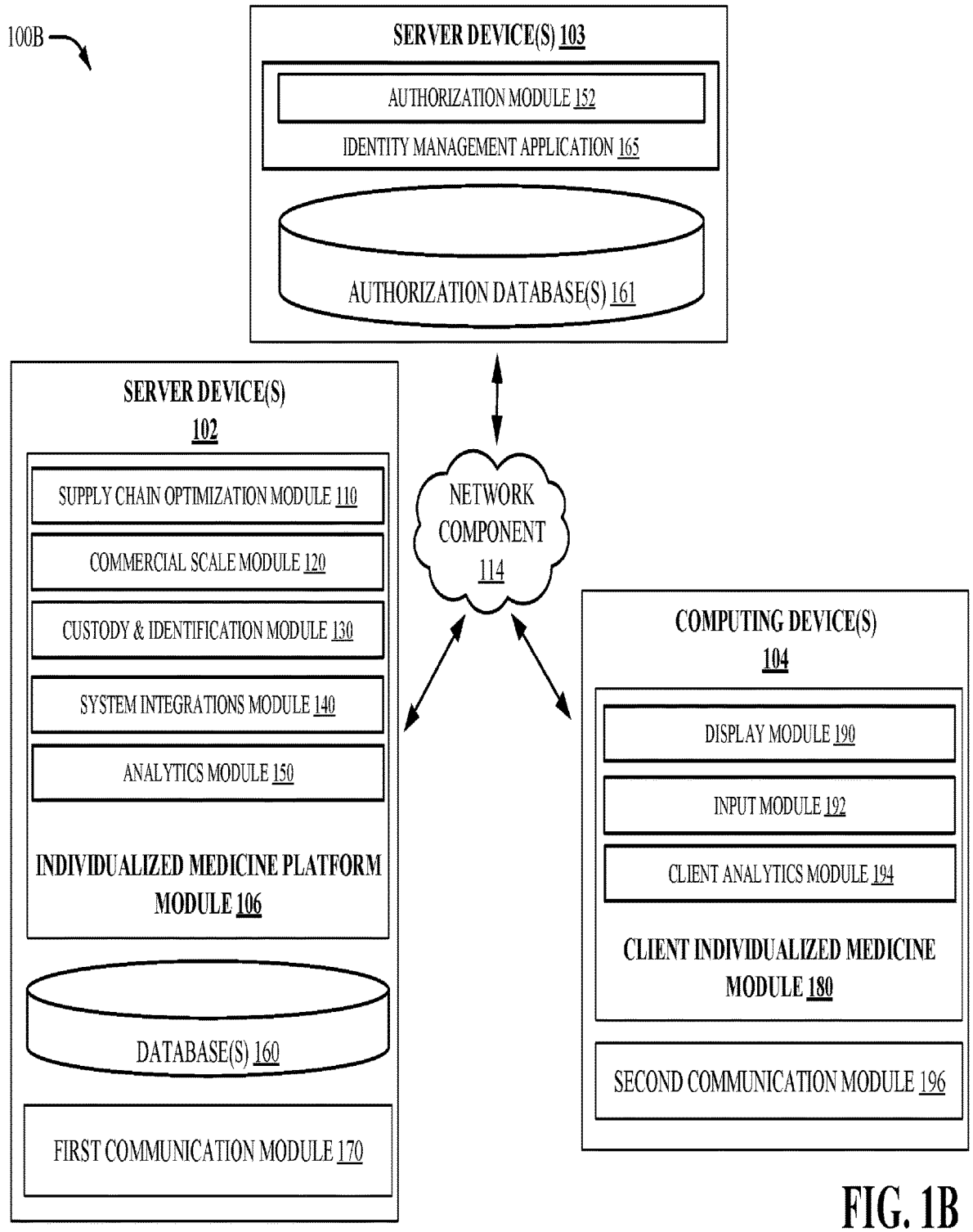
FIG. 1B illustrates an example, non-limiting block diagram of a representative environment 100B in which a user management, credential management, custom role and permission management, and role to permission mapping is executed by an individualized medicine platform and internal authorization system in accordance with one or more embodiments described herein.

Turning now to FIG. 1B, illustrated is an example environment 100B in accordance with one or more implementations. In various implementations, the example described with respect to FIG. 1B can be considered a continuation of the example described in FIG. 1A. Repetitive description of like elements employed in other embodiments described herein is omitted for sake of brevity. FIG. 1A illustrates an example, non-limiting environment 100A in which the individualized medicine platform module 106 can execute operations that include user management, credential management, custom roles management, permission management, mapping role to permissions, and other supply chain operations disclosed in FIG. 1A.

In an aspect, FIG. 1B discloses the components and devices illustrated in FIG. 1A and further discloses server device(s) 103 that executes identity management application 165 that further employs authorization module 152. Furthermore, server device(s) 103 can include authorization database(s) 161. According to a non-limiting embodiment of environment 100B, the execution of the entire user management, credential management, custom roles and permission management, and role to permission mapping operations can be performed by individualized medicine platform module 106 and identity management application 165. In an aspect, individualized medicine platform module 106 can execute onboarding and identity administration actions such as creating user profile data (e.g., pharmaceutical client data or site user data), creating role data, assigning permission criteria to a role, and assigning a role to respective user profiles.

In another aspect, individualized medicine platform module 106 can employ database(s) 162 to store user profile data (e.g., pharmaceutical user profile data and site user profile data), role data (e.g., a role can connect a group of permissions to a context which defines the scope of the permission within a context of a respective therapy or region or if no context is considered then no scope within a terapy or region exists), permission criteria assigned to such role data (e.g., permitted operations or actions for execution by such user profile and role, where a permission can comprise of a step and action mapped to a role to which users can be added), action (e.g., an operation performed by a user device such as viewing, editing, deleting, eSigning, etc.), feature (e.g., a resource or entity or field configured to execute an action such as an order to create, order to approve, patient ID field, etc.) and grant record (e.g., correlates a permission step with an effective date of record as to when a permission was granted to a feature or step).

In an aspect, role data can include metadata such as PHI access and can be configured to map a permission model of individualized medicine platform module 106 to a group stored at identity management application 165. Furthermore, a therapy can represent a commercial or clinical product for which a respective supply chain is established, and a role can be attached to a respective therapy. In another aspect, a user can represent a user device (e.g., computing device(s) 104) that accesses the individualized medicine platform module 106 on behalf of an institute (e.g., hospital, manufacturer, etc.)

In another aspect, identity management application 165 (e.g., authentication provider) can execute a range of tasks including creating pharmaceutical user credentials and/or site user credential data, create groups (e.g., a set of user roles with access to an instance of permissions and rights) such as a development operation group which may be prohibited from accessing customer instances and/or a customer support group which may have permission to access customer's instances (e.g., or realm of functions) to execute maintenance operations, assignment of users (e.g., user profiles) to group data, and/or execute authentication operations. In an aspect, individualized medicine platform module 106 can have one or more instance of applications executed by the platform module, each such instance capable of correspondence to a respective instance database. Furthermore, each instance can store user profile data for user access to such respective instance and a user profile can be stored in (and provide access to) multiple platform module applications.

Furthermore, in an aspect, authorization database(s) 161 can store user credential data for all user profiles across individualized medicine platform module 106 and group data corresponding to all user profiles across individualized medicine platform module 106. In another aspect, identity management application 165 can be configured to execute authorization operations for all users (e.g., pharmaceutical client users, other platform and website users, customer support users, etc.). Furthermore, identity management application 165 can be configured to execute development operations tasks such as creating customer realms, creating client configurations, creating user profiles, assigning groups to user profiles, generating default rules and policies, federating customer realms for customer success groups and development operations groups, creating administrative access tokens (e.g., for application processing interface (API) actions, and/or creating AuthN token.

In an aspect, such embedded identity provider exemplified by environment 100B can include all users within individualized medicine platform module 106. Furthermore, environment 100B configures individualized medicine platform module 106 as a service provider (e.g., consortium of web applications, storage services, applications that enable users and/or systems to perform respective tasks) and identity management application 165 is configured as an identity provider (e.g., executes authentication and authorization tasks).

In a non-limiting embodiment, computing device(s) 104 may represent a pharmaceutical client who seeks to rely on server device(s) 103 to execute all authentication operations (e.g., user management, credential management, management of custom roles and permission management, mapping of roles to permissions, etc.). As such, identification management application 165 can authorize all users (e.g., pharmaceutical users, platform users, customer support users, etc.) utilizing individualized medicine platform module 106 in furtherance of the goals related to procurement and administration of the pharmaceutical company personalized therapy. Furthermore, any system and/or application integrated (e.g., using system integrations module 140) with individualized medicine platform module 106 can also utilize identity management application 165 to execute operations related to the pharmaceutical client therapeutic.

For instance, a manufacturer seeking to transmit schedule availability information for manufacturing or transmit real-time manufacturing data related to a pharmaceutical client therapeutic medicine can be authenticated (e.g., identified as an authorized user, provided a group of permissions associated with a respective authorized role, etc.) by identity management application 165 with respect to target activities, respective therapies, a target region, and/or a global context designation (e.g., no permissions associated with any particular therapy or region). In an instance, an authorized role can indicate whether a user has access to respective subsets of metadata such as PHI data. Furthermore, individualized medicine platform module 106 can generate and store permissions such as a permitted step (e.g., a resource, entity, or field upon which a user can take an action) and action (e.g., an operational activity such as creating an order, approving an order, etc.).

Also, such permissions can be mapped to role data stored at server device(s) 103 (e.g., authorization database(s) 161).

As such, an authentication operation performed by identity management application 165 can facilitate (via mapped permissions) user devices initiating execution of authorized activities by individualized medicine platform module 106. In an instance, environment 100B can allow for convenience, speed and flexibility of authentication mechanisms for client devices. For instance, a pharmaceutical client device need not manage any authentication activities across an assortment of users spread across various entities. Instead, identity management application 165 can provide a single system for execution of authentication operations for an assortment of user devices representing different entities (e.g., cryogenic storage facilities, manufacturers, couriers, lab technicians, hospitals, pharmaceutical company, etc.) operating on a single therapy.

Figure 1C:
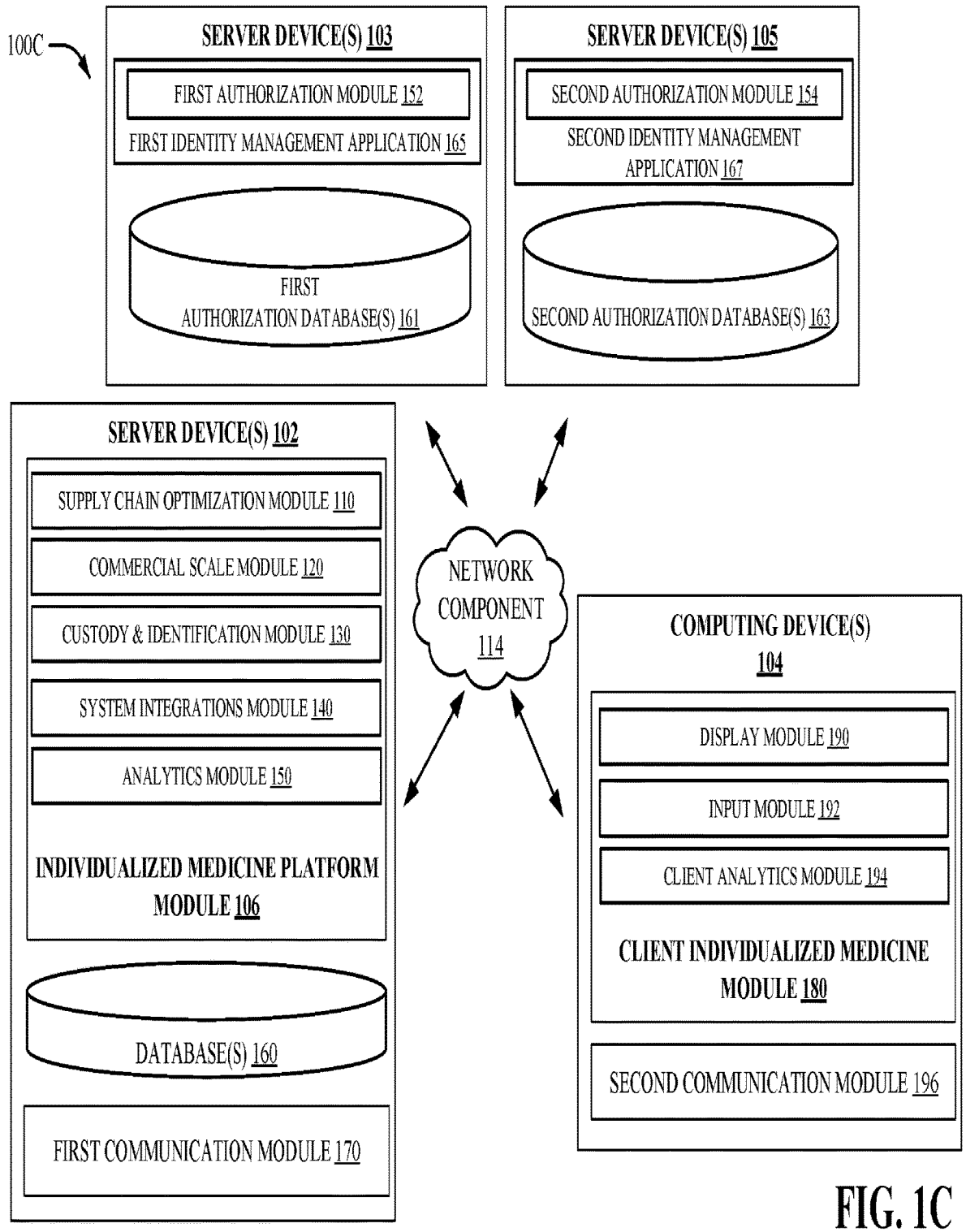
FIG. 1C illustrates an example, illustrates an example, non-limiting block diagram of a representative environment 100C in which a user management, credential management, custom role and permission management, and role to permission mapping is executed by an individualized medicine platform, internal authorization systems and external authorization systems in accordance with one or more embodiments described herein.

Turning now to FIG. 1C, illustrated is an example environment 100C in accordance with one or more implementations. In various implementations, the example described with respect to FIG. 1C can be considered a continuation of the example describe in FIG. 1A and include elements of FIG. 1B. Repetitive description of like elements employed in other embodiments described herein is omitted for sake of brevity. FIG. 1A illustrates an example, non-limiting environment 100A in which the individualized medicine platform module 106 can execute operations that include user management, credential management, custom roles management, permission management, mapping role to permissions, and other supply chain operations disclosed in FIG. 1A and FIG. 1B.

In an aspect, FIG. 1C discloses the components and devices illustrated in FIG. 1A and FIG. 1B and further discloses server device(s) 105 configured to execute second identity management application 167 and store data in second authorization database(s) 167. According to a non-limiting embodiment of environment 100C, the execution of various operations can be performed by respective devices. For instance, individualized medicine platform module 106 can execute user profile management tasks, custom role and permission management tasks, and role to permission mapping tasks. Furthermore, intermediary authentication operations can be executed by first identity management application 165. Also, user credential management operations can be executed by second identity management application 167, user profile data stored within database(s) 160, and user credential data stored within second authorization database(s) 163.

As such, in a non-limiting embodiment of environment 100C, individualized medicine platform module 106 can be configured as a service provider, first identity management application 165 can be configured as a service provider and second identity management application 167 can be configured as an identity provider. In some instances, the identity provider can be a third-party integration or internal identity provider integration within the environment. In another aspect, the identity provider can be characterized as a single sign on provider. In some instances, environment 100C can include pharmaceutical and site users within identity management application 167 and platform administrators can be included within the individualized medicine platform module 106 portion of the environment 100C.

As an example, within environment 100C, a user device representing an onboarding user or identity administrator can facilitate execution (e.g., using individualized medicine platform module 106) of one or more of actions such as importing client (e.g., pharmaceutical or site user) user data from server device(s) 106 (including applications and databases), qualifying imported user data, completing profiles for imported users, creating roles and corresponding such roles with respective identity providers (e.g., second identity management application 167) and target group names within respective identity providers, assigning permissions to roles, and/or assigning roles to users. In an aspect, database(s) 160 can store user profile data (e.g., for pharmaceutical client and site users), role data, permission data and requirements, action data, and/or grant data.

In another aspect of environment 100C, individualized medicine platform module 106 can execute one or more actions including requesting authentication from server device(s) 103, importing user data from server device(s) 105 (e.g., second authorization database(s) 163), and/or retrieving a group list from server device(s) 105 (e.g., second authorization database(s) 163). Accordingly, server device (s) 103 can execute first identity management application 165 configured to employ first authorization module 152 to act as an intermediary authentication provider for individualized medicine platform module 106 and authenticate developer operations users and customer support users. Furthermore, first identity management application 165 can be configured to execute actions on behalf of development operators such as creating customer realms, creating client configurations, creating federation configurations, setting default policies (e.g., client-customizations), federating customer success realms, and/or creating administrative access tokens (e.g., for API access by respective applications and integrations). Also, first authorization database(s) 161 can be configured to store federation configuration information and user credential data for individualized medicine platform module 106 users.

In an aspect, the federation functionality disclosed in environment 100C allows for the selection of a user stored in a third-party identity service provider (e.g., server device (s) 105). For instance, a client identity administrator user can access individualized medicine platform module 106 to create a user role (e.g., based on therapy and region context), however, where the role is mapped to an external or third party provider (e.g., server device(s) 105, second authorization database(s) 163), the devices and systems in environment 100C can integrate with such external providers via the federated mechanism disclosed herein. In a non-limiting aspect, a role can be mapped to one external identity service provider (e.g., second identity management application 167) and can be cloned to associate with a second identity service provider. In other non-limiting embodiments, multiple external identity service providers can be integrated. In an aspect, individualized medicine platform module 106 can request (e.g., query) group data from second authorization database (s) 163 based on permission provided from a user profile to request such group data. Furthermore, in another non-limiting embodiment, individualized medicine platform module 106 can test the existence of group data stored at second authorization database(s) 163 or create group data within second identity management application 167 for storage within second authorization database(s) 163 based on access grants and permissions.

In yet another aspect, environment 100C can employ first identity management application 165 to authorize second identity management application 167 to execute authentication activities for all users (e.g., pharmaceutical client users, site users, etc.) and execute actions by a clients' identity administrator (e.g., create users, create groups, assign users to groups, create application profiles such as SAML profiles, create authN tokens, etc.). In another aspect, second authorization database(s) 163 can store user credentials for respective users (e.g., pharmaceutical client users, site users, etc.), and/or group data.

In another non-limiting embodiment, environment 100C can also allow some clients (e.g., pharmaceutical users, site users, etc.) to execute operations such as user profile management, credential management, role and permission management, role to permission mapping using individualized medicine platform module 106 and store user data and credential data within first identity management database 161. In such embodiment, the individualized medicine platform module 106 is configured as a service provider and server device(s) 103 is configured as an identity provider.

In other non-limiting embodiments, the user credential management operations can be executed by server device(s) 105, an external identity provider. In such non-limiting embodiment, server device(s) 103 is configured as an intermediary or bridge component also acting as a service provider (along with individualized medicine platform module 106). In such scenario's all pharmaceutical client and site user profile data are configured for storage with database(s) 160. As such, the user profiles are qualified and correlated to respective sites and therapies.

In such non-limiting embodiment, environment 100C provides several advantages and architectural improvements and improvements to computing devices. For instance, environment 100C allows for the performance of authentication activities in relation to individualized medicine platform module 106 in a flexible and robust manner. In an instance, individualized medicine platform module 106 may be accessed and conduct operations pursuant to client devices (e.g., computing devices 104) corresponding to several independent clients such as pharmaceutical clients, hospitals, centers of excellence, and other such clients. In an aspect, each client may have authentication preferences, such as utilizing an internal IDP store (e.g., server device(s) 105) to authenticate a group of users (e.g., pharmaceutical users) and another IDP store (e.g., server device(s) 103) to authenticate another group of users (e.g., hospitals, manufacturers, other users of individualized medicine platform module 106).

As such, non-limiting embodiments represented by environment 100C can be allow for flexibility in authentication mechanisms (e.g., allowing for platform authentication and independent client authentication mechanisms to operate in an integrated environment), improve the speed of deploying authentication operations with respect to various client users (e.g., allowing for platform authentication and independent client authentication mechanisms to execute in an unhampered manner to one another in an integrated environment and eliminating the need to replicate data such as authentication data over several instances thus enhancing processing speeds), enhancing the security of the system (e.g., a nurse at a hospital can login through the hospital system and still be authenticated for use of the individualized medicine platform module 106, so less security vulnerabilities due to only needing one set of credentials across systems), and other such improvements and advantages. Furthermore, the system security is further enhanced such that offboarding a user does not require the removal of user credentials from several IDP systems (which is error prone) but rather requires credential removal from a single system to in the event an offboarding event occurs (e.g., nurse is retiring from a hospital, etc.).

In an instance, environment 100C facilitates a multi-tenant authentication model such that client devices associated with a range of users operating on a single therapy can utilize a range of IDP systems to perform authentication operations and allow various user devices to access and execute operations associated with to several operational instances associated with individualized medicine platform module 106. For instance, second identity management application 167 can authenticate a nurse in a San Francisco hospital to work on two therapies associated with different pharmaceutical providers but requiring a single authentication activity by identity management application 167. Furthermore, in a range of non-limiting embodiments, first authorization database(s) 161 and second authorization database(s) 163 can authenticate different subsets of users and/or user devices.

For instance, in a non-limiting embodiment that represents a federation configuration, database(s) 160 can store user profile data for all users of platform module 106, all pharma users, all role data, all permission data, all action data, and all grant data. Furthermore, first authorization database(s) 161 can store user credentials for some pharmaceutical clients, site clients, and platform module 106 users, and group data for some pharma clients, and site users. Also, second authorization database(s) 163 can store user credential data for some pharmaceutical users and site users, and some group data. As such, the system allows for integration of third party IDP's associated with a subset of clients and internal IDP's associated with platform module 106.

In another non-limiting embodiment represented a full federated configuration, first authorization database(s) 161 can store user credentials for all platform module 106 users and second authorization database(s) 163 can store user credentials for all pharmaceutical client devices and site user devices. As such, a different configuration of authentication for respective entities is enabled via such embodiment. Accordingly, environment 100C allows for the deployment of a flexible authentication mechanism in association with several users executing operations on several therapies. Furthermore, environment 100C allows for a faster (e.g., enhances processing time of authentication data by eliminating redundant data) system, more secure (e.g., provides a single authentication point for users depending on the user device) system, and improved system efficiency as compared to traditional authentication mechanisms. As such, environment 100C allows client devices to keep existing IDP mechanisms and manage fragmented IDP mechanisms (via integrating with platform module 106), simultaneously employ new authentication mechanisms, and allow user devices to operate across multiple entities and access multiple channels to effectuate generation and deployment of individualized therapeutic medicines.

For instance, Pharmaceutical Company A IDP, Pharmaceutical Company B IDP, Hospital C IDP, and first identity management application 165 can be integrated via environment 100C and authorize Pharmaceutical Company A (Pharma A device), Pharmaceutical Company B (Pharma B device), Hospital C (Hospital C device), to access respective customer instances. For instance, Pharma A device and Hospital C device can access customer A instance (e.g., ordering, collection, manufacturing, etc.) of activities corresponding to a therapy as employed by individualized medicine platform module 106. Furthermore, Pharma B device and Hospital C device can access customer B instance (e.g., ordering, collection, manufacturing, etc.) of activities corresponding to another therapy as employed by individualized medicine platform module 106.

Accordingly, environment 100C can accommodate a multitude of scenarios to integrate external IDP's and internal IDP's (e.g., first identity management application 165) with individualized medicine platform module 106. In a non-limiting embodiment, one or more client (e.g., using computing device(s) 104) can integrate its own IDP system that authenticates internal (e.g., pharmaceutical company users) and external users (e.g., hospitals, manufacturers, etc.) with individualized medicine platform module 106. In another non-limiting embodiment, one or more client (e.g., using computing device(s) 104) can integrate its own IDP system that authenticates internal (e.g., pharmaceutical company) users only with individualized medicine platform module 106 and allow first identity management application 165 to authenticate all other users. In yet another non-limiting embodiment, based at least on security considerations, one or more client (e.g., using computing device(s) 104) can integrate its own IDP system that authenticates internal users (e.g., pharmaceutical company) and manufacturing users only with individualized medicine platform module 106 and allow first identity management application 165 to authenticate all other users (e.g., a multitude of clinics, hospitals, etc.).

Also, a non-limiting embodiment can include, one or more client relying on first identity management application 165 to authenticate all users and no internal IDP system is integrated. In such embodiment, first identity management application 165 can provision multi-factor authentication operations. In yet another non-limiting embodiment, one or more client (e.g., hospitals, clinics, etc.), using computing device(s) 104, can utilize one set of credentials to access all personalized therapies (e.g., across all pharmaceutical clients). Furthermore, in a non-limiting embodiment, one or more client (e.g., contract manufacturers), can utilize first identity management application 165 to authenticate all manufacturing related users to perform operations (e.g., using individualized medicine platform module 106) related to manufacturing for all clients (e.g., pharmaceutical companies).

In another non-limiting embodiment, once a user device or user profile is authenticated, then an authorization module can determine the therapies and corresponding pharmaceutical company a user is qualified to access, the respective pharmaceutical instance accessible to the user, and the users' role each customer can access. In an aspect, a user can be authenticated and authorized to access a particular role specific to a respective instance such that even if a user is authorized to access multiple customer instances, each session can restrict a user's access to a single customer for such session. For example, a hospital provider user may view a list of orders associated with various customer instances and a selection of a respective order can permit access into that respective order for a costumer's instance. In another example, an apheresis nurse user can select a patient from a collection of patients each associated with a respective customer instance.

Figure 1D:
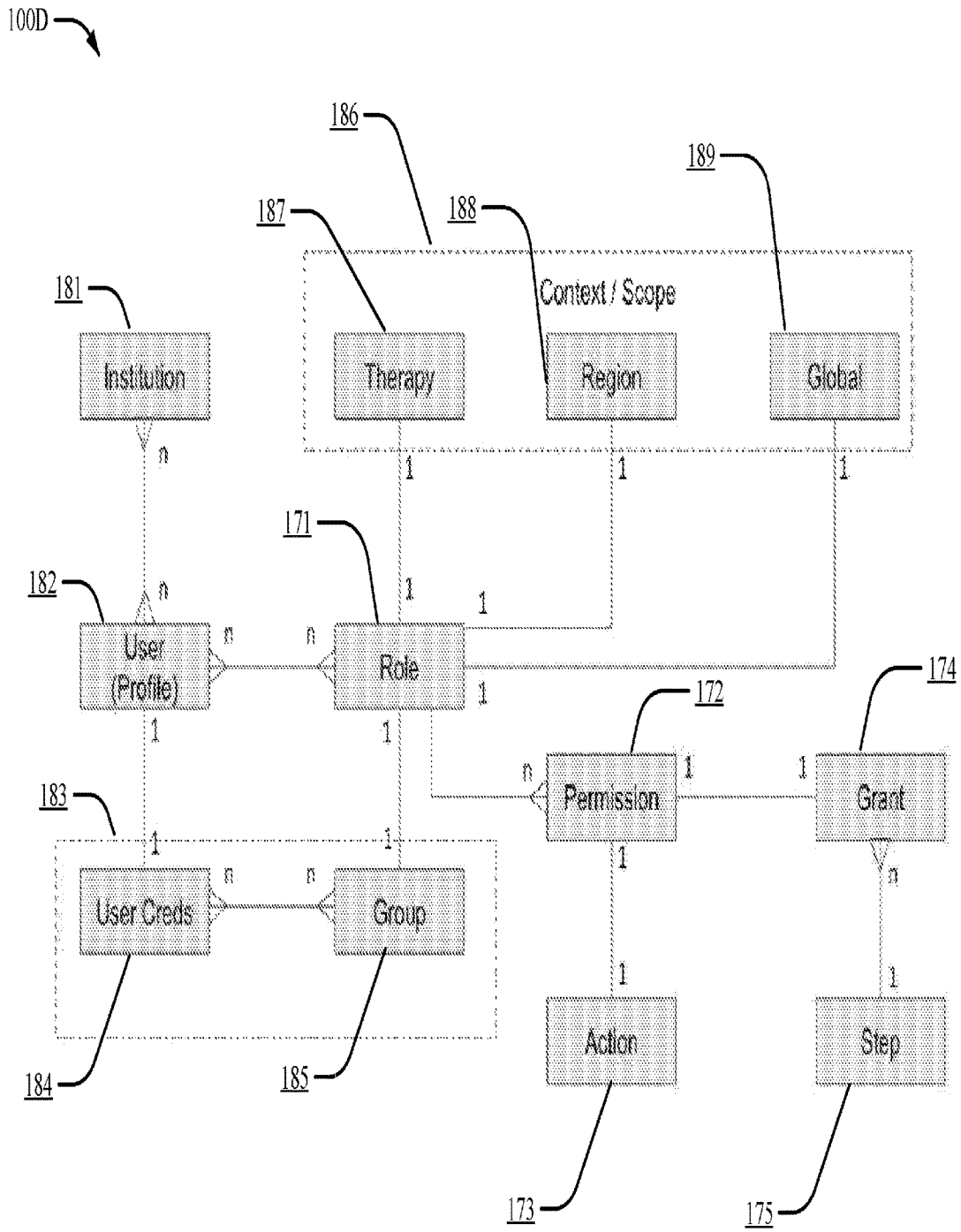
FIG. 1D illustrates an example, non-limiting block diagram of an entity relationship model associated with an individualized medicine platform in accordance with one or more embodiments described herein.

FIG. 1D illustrates an example, non-limiting block diagram of an entity relationship model associated with an individualized medicine platform in accordance with one or more embodiments described herein. Repetitive description of like elements employed in other embodiments described herein is omitted for sake of brevity. In an aspect, reference numeral 183 represents an identity provider device (e.g., server device(s) 103 and/or server device(s) 105) which can be represented by different device(s) depending on the environment and model deployed (e.g., embedded vs. federated). At reference numeral 184, user credential data (e.g., login id and password) and/or group data (e.g., reference numeral 185) can be configured for storage at a database of the device represented by reference numeral 183.

Furthermore, in an aspect, reference numeral 173 can represent an action (e.g., action requested by computing device(s) 104 and executed by server device(s) 102 and respective modules) such as a request to view, create, edit, delete, eSign, and other such action. At reference numeral 175, disclosed is a step configured as a resource, entity, or field, by which a computing device(s) 104 can take an action or initiate an action request. At reference numeral 172 is a permission comprising one or more collective permissions configured as a step and action collectively. At reference numeral 174 is a grant that connects a group of permission to a context that can be based on a therapy and/or region. A therapy (e.g., reference numeral 187) can represent a commercial or clinical product for which the supply chain is established.

At reference numeral 171 is a role which connects a group of permissions to a context (e.g., therapy or region). In an aspect, reference numeral 188 represents a region such as a country or world region (e.g., European Union, USA, etc.) which may correspond to one or more separate instance in order to satisfy residency requirements associated with the supply chain, regulatory compliance, and/or supply chain practicalities. At reference numeral 189 is a global context, indicating that the role is not scoped by any respective therapy or region. At reference numeral 186 is an indication that depending on the environment deployed, the reference numerals 187, 188, and 189 can be stored on the same or separate device(s) as indicated by reference numeral 186. At reference numeral 182 is a user profile data or an entity user from an institute (e.g., reference numeral 181) to perform an action (e.g., reference numeral 173) on a step (e.g., reference numeral 175) for a therapy (e.g., reference numeral 187) in a region (e.g., reference numeral 188). At reference numeral 181 is an institution also referred to as a site that represents locations from where computing device(s) 104 can access individualized medicine platform 106. As an example, an institution can be a center of excellence and/or manufacturing facility. Users are associated with institutions.

Figure 1E:
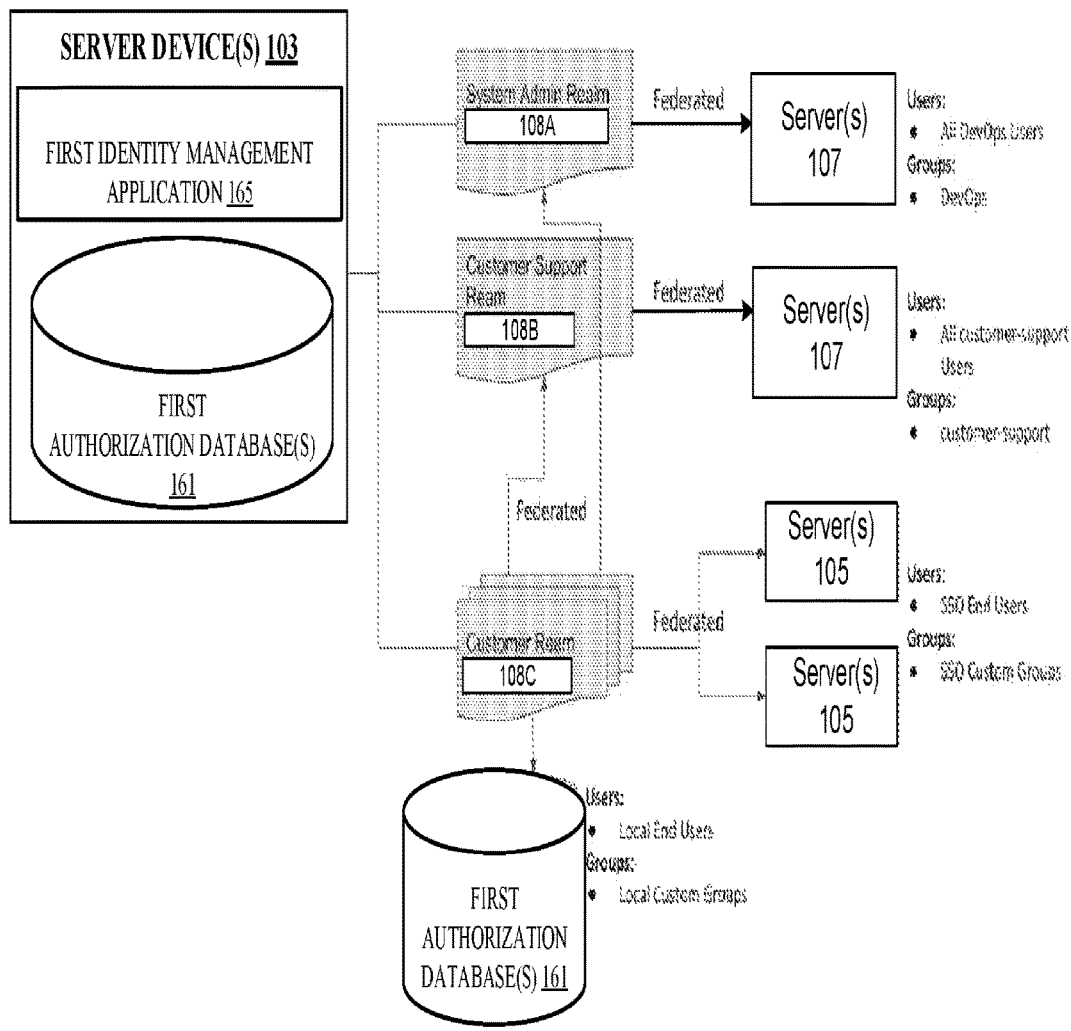
FIG. 1E illustrates an example, non-limiting block diagram of an interactive relational model corresponding to a federated model and associated environment in accordance with one or more embodiments described herein.

FIG. 1E illustrates an example, non-limiting block diagram of an interactive relational model corresponding to a federated model and associated environment in accordance with one or more embodiments described herein. Repetitive description of like elements employed in other embodiments described herein is omitted for sake of brevity.

In an aspect, a single sign on architecture can be employed amongst the individualized medicine platform module 106 and affiliated entities. Many sites (e.g., manufacturer, centers of excellence, etc.) are common between varying client users (e.g., pharmaceutical companies) such that having the same login access credentials among various application instances creates system, device-oriented, and environmental efficiencies (e.g., bandwidth enhancement, decreased processing expense, etc.). In one or more non-limiting embodiment, server device(s) 107 can be employed to onboard shared user profiles and devices belonging to a common organization. In an aspect, respective instances can be configured to groups of customer or particular users by deploying realms. In an aspect, a realm can be a shared subsystem for a group of users to access a respective instance of functionality. As an example, a development operations realm can comprise users assigned such roles and corresponding groups with access to such respective instances.

As such, server(s) 107 can be configured as a source of truth for employees of the individualized medicine platform module 106 (e.g., development operations staff, customer support staff or technical support staff. As such realm 100A and realm 100B can be configured as a source of credentials for development operator users and customer support users respectively. Furthermore, in an aspect, realm 108C can be configured as a customer realm configured for customer user (e.g., manufacturer, pharmaceutical company, etc.) to execute respect operations. Customers can also restrict various permissions by other groups in some instances.

Figure 2:
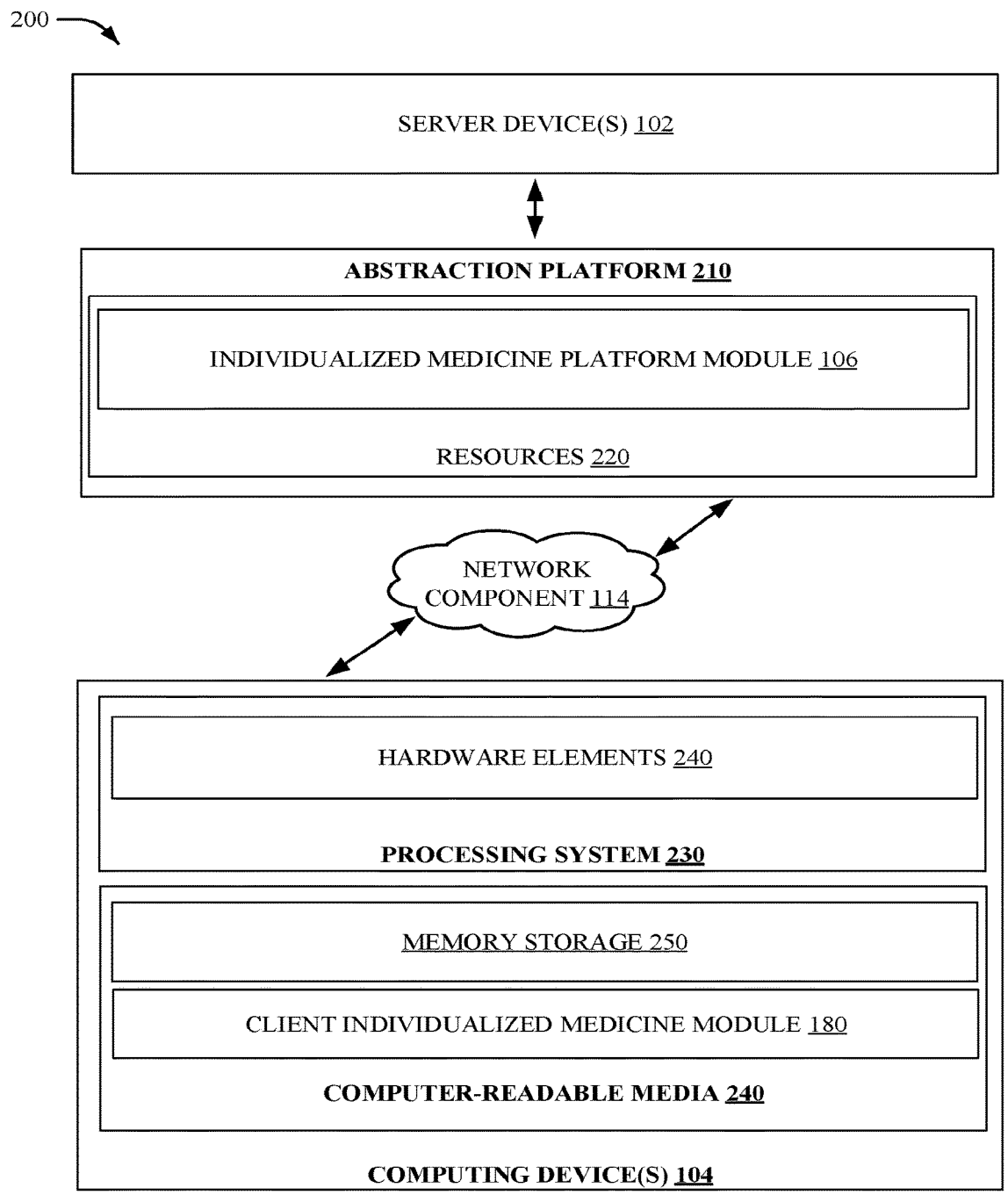
FIG. 2 illustrates an example, non-limiting environment in which cloud-based services can be used to provide features corresponding to events and activities associated with a personalized medicine supply chain in accordance with one or more embodiments described herein.

Turning now to FIG. 2, illustrated is an example environment 200 in accordance with one or more implementations. In various implementations, the example described with respect to FIG. 2 can be considered a continuation of the example describe in FIG. 1A. Repetitive description of like elements employed in other embodiments described herein is omitted for sake of brevity. FIG. 2 illustrates an example, non-limiting environment 200 in which cloud-based services can be used to provide features corresponding to events and activities associated with a personalized medicine supply chain in accordance with one or more embodiments described herein. In an aspect, environment 200 can include server device(s) 102, computing device(s) 104, and network component 114, where computing device(s) 104 includes a processing system 230, and one or more computer-readable media 240.

In an aspect, processor 230 can comprise one or more processor configured to perform one or more operations (of at least one module of client individualized medicine module 180) using hardware. As such, processor 230 can include hardware components 240 that may be configured as processors, functional blocks, and so forth. This may include implementation in hardware as an application specific integrated circuit or other logic device formed using one or more semiconductors. In an aspect, the hardware components 240 are not limited by the materials from which they are formed or the processing mechanisms employed by such materials. For example, processors may be comprised of semiconductor(s) and/or transistors (e.g., electronic integrated circuits). In such a context, processor-executable instructions may be electronically-executable instructions.

The computer-readable media 240 is illustrated as including memory storage 250. The memory storage 250 represents memory storage capacity associated with one or more computer-readable media. The memory storage 250 may include volatile media (such as random access memory (RAM)) and/or nonvolatile media (such as read only memory (ROM), Flash memory, optical disks, magnetic disks, and so forth). The memory storage 208 may include fixed media (e.g., RAM, ROM, a fixed hard drive, and so on) as well as removable media (e.g., Flash memory, a removable hard drive, an optical disc, and so forth). The computer-readable media 240 may be configured in a variety of other ways as further described below. In an aspect, client individualized medicine module 180 of FIG. 1 is illustrated as residing within memory storage 250, but alternate or additional implementations can implement client individualized medicine module 180 using combinations of firmware, hardware, and/or software without departing from the scope of the claimed subject matter, such as hardware components 240.

Example environment 200 enables multiple devices to be interconnected through server device(s) 102, where server device(s) 102 can be local to the multiple devices, remote from the multiple devices, or any combination thereof. In one or more implementations, server device(s) 102 can be configured as a cloud of one or more server computers that are connected to the multiple devices through a network (e.g., using network component 114), the Internet, or other data communication link capable of enabling functionality to be delivered across multiple devices (e.g., several smartphone devices, desktops, tablets, etc.) to provide a common and seamless experience to a user of the multiple devices. Each of the multiple devices may have different physical requirements and capabilities, and the central computing device uses a platform to enable the delivery of an experience to the device that is both tailored to the device and yet common to all devices. In a non-limiting embodiment, a class of target devices having unique physical features, types of usage or other such characteristics can be deployed, and tailored user experiences can be implemented on such class of generic class of devices.

In an aspect, cloud computing network or network component 114 can include or represent an abstraction platform 210 for resources 220. In another aspect, the abstraction platform 212 abstracts underlying functionality of hardware (e.g., servers) and software resources of the cloud 210. In an aspect, resources 220 may include applications and/or data that can be utilized while computer processing is executed on servers (e.g., server device(s) 102) that are remote from the computing device(s) 104. For example, resources 220 can include individualized medicine platform module 106 at FIG. 1A. In another aspect, the abstraction platform 210 may abstract resources and functions to connect computing device 104 with other computing devices and may also serve to abstract scaling of resources to provide a corresponding level of scale to encountered demand for the resources 220 that are implemented via the abstraction platform 210. Accordingly, in an interconnected device embodiment, implementation of functionality described herein may be distributed throughout the system. For example, the functionality may be implemented in part on the computing device 104 as well as via the abstraction platform 210 that abstracts the functionality of the network component 114.

In another aspect, abstraction platform 212 can allow for external system integrators to keep data private on individualized medicine platform module 106, while abstraction platform 210 can extract learnings from such data to educate a range of machine learning algorithms. For instance, hyper-parameters of machine learning models applied to a first external device data can be extracted and the hyper-parameters can be applied to data of a second external device. As such, learnings from analyzing and curating a first client data can be applied to the analysis and curation of a second client data without ever exposing the private data of each user.

Figure 3:
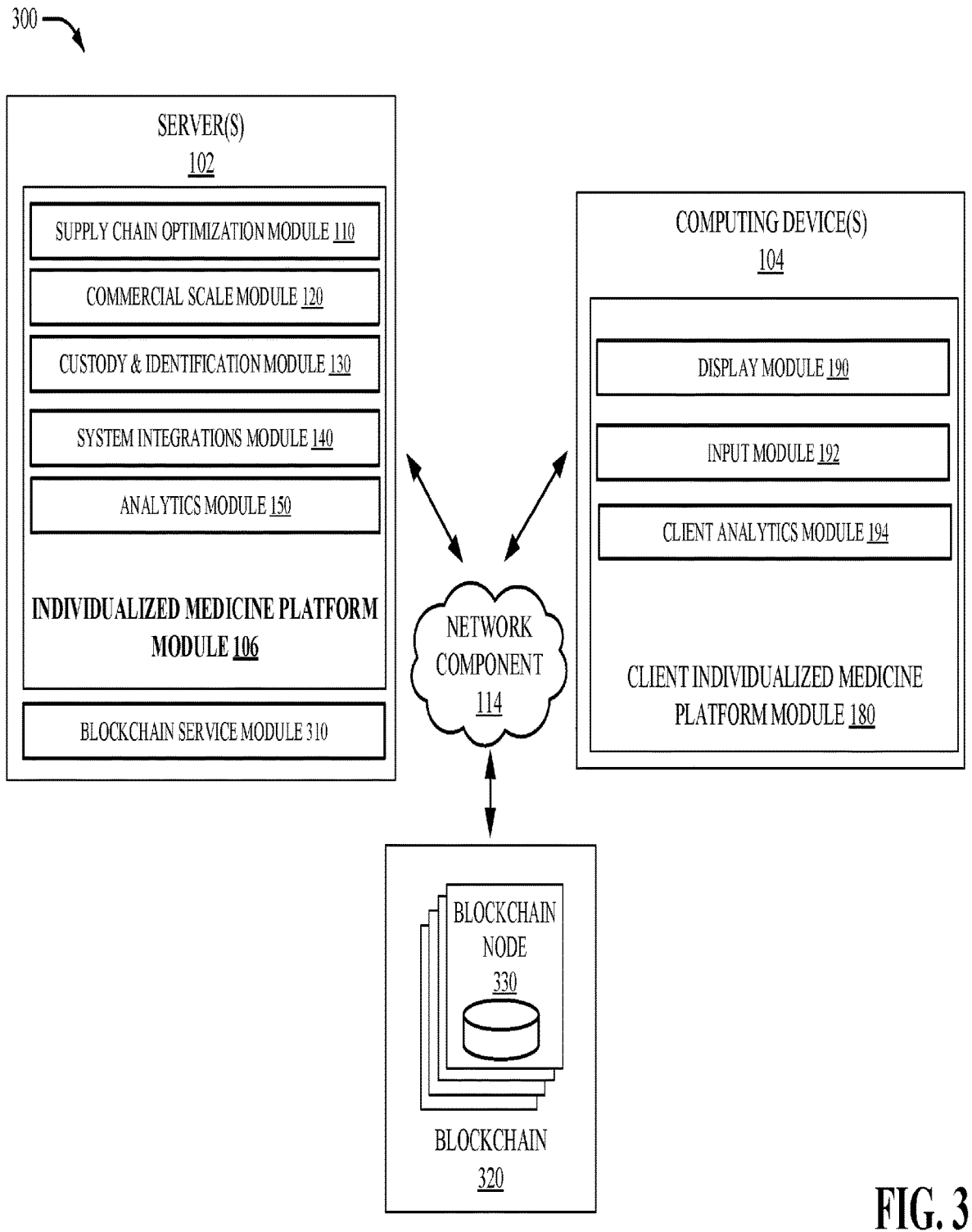
FIG. 3 illustrates an example, non-limiting system that includes a personalized medicine supply chain platform that interfaces with a blockchain in accordance with one or more embodiments described herein.

Having described example operating environments in which various aspects of individualized platform module 106 can be implemented, consider now a discussion of generating a blockchain in accordance with one or more implementations of FIG. 1A and FIG. 2 and the subject matter disclosed herein. Turning now to FIG. 3, illustrated is an example, non-limiting system that includes a personalized medicine supply chain platform that interfaces with a blockchain in accordance with one or more embodiments described herein. Repetitive description of like elements employed in other embodiments described herein is omitted for sake of brevity.

In a non-limiting embodiment, the systems disclosed in environment 100A of FIG. 1A and environment 200 of FIG. 2 can be configured to communicate and/or integrate with a distributed blockchain system (disclosed in FIG. 3) comprising multiple computing nodes, such that each computing node is configured to store a copy or a portion of a blockchain. In some instances, a blockchain 320 may be used to store data associated with individualized medicine platform module 106. Furthermore, in an aspect, blockchain 320 can be a distributed database that maintains a continuously updated list of records, where each the updated list of records can be stored on blocks linked together as a chain. In an aspect, the blocks can be secure storage vehicles (e.g., encryption based on public-key and private-key pairings) and are immutable (cannot be changed).

In another aspect, the blockchain can record a transaction (e.g., a transfer of information onto, from or with individualized medicine platform module 106) within a ledger database of the blockchain that is shared by devices participating in a distributed network of computers. In yet another aspect, the distributed ledger can present a consensual (by all computers within the distributed network) record corresponding to a cryptographic audit trail that is validated and maintained by independent computers. In yet another aspect, blockchain 320 can employ a network of blockchain nodes 330 that can support the blockchain, which may include a set of blocks that store data corresponding to individualized medicine platform module 106.

In an aspect, data stored on nodes of blockchain 320 can include transactional data (e.g., event data, identifier data, etc.) acquired, generated, curated, transformed, and/or received by individualized medicine platform module 106. In a non-limiting aspect, the data can be transmitted (e.g., using blockchain service module 310) as duplicate data to a blockchain system employing blockchain 320. In another non-limiting aspect, the data can be transmitted to the blockchain system as original data (non-duplicate data), such that the blockchain system serves as a primary data store for one or more sets of data. In an embodiment, only the additional data in a transaction (not including the previously transmitted duplicate data) can be transmitted for incorporation onto the blockchain. As such, the blockchain can be configured to store data corresponding to the data of individualized medicine platform module 106. In an aspect, blockchain 320 is a data structure that stores a list of transactions. In an aspect, blockchain 320 can be a distributed electronic ledger that records transactions between various stakeholders (e.g., providers, patients, centers of excellence, healthcare providers, couriers or third-party logistics providers, manufacturers, suppliers, cryogenic storage facilities, administrative managers, and other such stakeholders) of the individualized medicine platform module 106. In one or more non-limiting embodiments, blockchain 320 can be a decentralized public (or private) transaction ledger that can be deployed over one or more node (e.g., server) and configured to perform transaction-based state transitions and smart contract functionality.

In a non-limiting implementation, computing device(s) 104 can interact with a server device(s) 102 configured to control one or more node (e.g., blockchain node 330 and other such nodes) of blockchain 320. In an aspect, server device (s) 102 can be configured to facilitate access to one or more node of blockchain 320. For instance, server device (s) 102 can control access to blockchain node 330 that represents an Ethereum blockchain or other distributed ledger node featuring transaction-based state transitions and/or smart contract functionality. In another aspect, a smart contract may be stored as a block with blockchain 320 and data included as components of the smart contract can be stored within separate blocks within the blockchain. Furthermore, in a non-limiting embodiment, each node of a blockchain 320 can store a copy of a smart contract program structures.

In an aspect, smart contracts can refer to computer programs or scripts (e.g., program structures) that are embedded into blockchain transactions and can be executed on blockchain 320. As a non-limiting example, a smart contract can represent a software program that automatically sends a monetary amount (e.g., a payment that represents a blockchain transaction, the payment can be a cryptocurrency, etc.) from a first digital wallet of a manufacturer (e.g., manufacturer of individualized therapeutic medicine) to a second digital wallet of a raw material supplier (e.g., of a raw material to make an individualized therapeutic medicine) upon receipt of the raw material at the manufacturer facility (e.g., as evidenced by signature data transmitted to the blockchain or courier confirmation of delivery of delivery of the raw material). In another aspect, blockchain service module 310 employed by server device(s) 102 can represent the provisioning of services associated with blockchain 320 (e.g., a group of blockchain nodes). In another aspect, individualized medicine platform module 106 can access blockchain services using blockchain service module 310 that can use remote procedure call conventions, service-oriented architectures, or other mechanisms that facilitate remote computer systems (e.g., individualized medicine platform module 106) to request services from remote resources (e.g., blockchain 320).

In an aspect, blockchain 320 can employ smart contracts that perform a transaction (e.g., exchange of currency) based on evidence of an occurrence of an event within an individualized medicine supply chain. In a non-limiting embodiment, the events that meet an evidentiary requirement of a smart contract can be trusted if such events represent data acquired from, transmitted from, or generated by individualized medicine platform module 106. Accordingly, a smart contract deployed within one or more node of blockchain 320 can include programmatic logic that requires only data representing events corresponding to a private key signature of individualized medicine platform module 106 (e.g., server device(s) 102) can be trusted to satisfy evidentiary requirements of the smart contract. Furthermore, in an aspect, the private key signature of individualized medicine platform module 106 represents that data or event data can be trusted by blockchain 320 and/or smart contract programmatic logic code.

In another non-limiting embodiment, each client device (e.g., representing a different customer using individualized medicine platform module 106) can correspond to its own respective digital wallet and its own blockchain. As such, a clear audit trail can be more transparent and allow for traceability of particular transactions of such client. Accordingly, a first block chain can correspond to a first client (e.g., raw material supplier) and a second block chain can correspond to a second client (e.g., a manufacturer). Furthermore, a combination of event data from the first blockchain and the second blockchain can be utilized by a smart contract stored on the first blockchain, the second blockchain or a third blockchain (that is separate from the first blockchain and the second blockchain) to facilitate transactions between clients. Furthermore, in a non-limiting embodiment, data (e.g., event, activity, identification data, etc.) corresponding with respective modules of individualized medicine platform module 106 can be stored on its own respective blockchain as well to facilitate data traceability audits, chain of identity audits, chain of custody audits and other such audits.

In a non-limiting embodiment, a programmatic logical code stored and executed on the block chain as a smart contract can represent execution of scheduling transactions based on scheduling condition data (e.g., scheduling appointments for apheresis and infusion activities based on factors that minimize the time between performing such activities such as location between facilities), transactions between manufacturers and entities contracting with manufacturers based on manufacturing capacity data and/or machine performance data (e.g., historical manufacturing performance data), perform route optimization tasks and execute logistic transactions based on route optimization determinations, performing re-route tasks based on real-time data and event data (e.g., deploy smart contract to allow for re-routing to occur upon the occurrence of various events), perform re-scheduling events (e.g., based on real-time data that indicate a party cannot satisfy contract requirements), select best manufacturing sites based on real-time data (e.g., machine performance or uptime data, manufacturers capacity data, past-performance data, quality scores of final product, etc.).

As a non-limiting example, a center of excellence (COE) such as a hospital or laboratory may request the manufacture of a therapeutic drug (to administer to a target patient) from any of multiple manufacturing facilities. Furthermore, in an aspect, each manufacturing site can manufacture therapeutic drugs intended for commercial use, clinical use, and in some instance use by a particular pharmaceutical company. In an aspect, each therapy may require a different standard operation procedure to effectuate proper manufacturing of the therapeutic medicine. In yet another aspect, a manufacturing facility (e.g., pharmaceutical site or contract manufacturing organization) has a maximum manufacturing capacity available to manufacture a particular therapeutic. Accordingly, the capacity can be a mixture of a reserved capacity for a therapy as well as an availability-based capacity determination. Furthermore, a raw material may be used to manufacture a personalized therapeutic medicine may undertake travel (e.g., raw material supplier, cryogenic storage facility, manufacturing facility, cryogenic storage facility, distribution facility, infusion site) prior to being shipped to an infusion site. For instance, a blood sample and corresponding cells may first undergo a collection process to analyze the sample and subsequently undergo a collection process before being transported to a manufacturing facility.

In an aspect, individualized medicine platform module 106 captures, generates, and curates data associated with the above logistics supply chain (e.g., ordering, collection, scheduling, capacity planning, etc.) and individualized medicine platform module 106 facilitates a coordination of activities between a COE and manufacturing sites as well as a patient based at least on scheduling constraint data. In a non-limiting embodiment, a capacity registry (curated by therapy, region, etc.) module can be implemented by individualized medicine platform module 106 to facilitate acquisition and aggregation of capacity data corresponding to each registered manufacturing facility. For instance, system integrations module 140 can receive published manufacturer capacity data from IVIES systems, supply chain optimization module 110 can receive manufacturer capacity data from manufacturer clients, and systems integration module 140 can acquire manufacturer machine data corresponding to capacity capabilities from internet of things (IOT) system integrations. Furthermore, individualized medicine platform module 106 can employ a smart router module to dynamically and communicatively connect centers of excellence to manufacturers via smart route determinations (e.g., based on capacity constraint data).

In another aspect, a smart router module can define rules governing each leg of a journey undertaken by a sample, intermediate product, and/or final product. For instance, a data set can represent a rule or set of instructions related to the pickup process at an apheresis site through the delivery process at an infusion site. In another instance, a data set can represent a rule or set of instructions that relate to which courier, storage facility, or manufacturer site can be selected along a route (e.g., based on a set of parameters). In an aspect, multiple types of routers can be employed by smart router module such as autologous vein-to-vein router, allogenic router, center of excellence router (e.g., establishes the optimum center of excellence for the patient's infusion based on resource constraints and commute distance), and a viral vector router representing a backend of supply. In another aspect, smart route determinations can be based on an optimization of manufacturing time and resources. Furthermore, systems integration module 140 can acquire relevant data from MES, MRP, machines, capacity planning modules, and other such data sources to facilitate optimal smart route determinations.

In a non-limiting embodiment, a smart route can be based on prioritization event data (e.g., such as proximity of manufacturer to a center of excellence, or a capacity availability at a manufacturer who may have a lower performance score than a facility with less capacity availability). In another aspect, smart router module can perform real-time smart routing determinations based on dynamic event data acquired by individualized medicine platform module 106. For instance, smart router module can perform a real-time smart routing adjustment based on a scheduled route no longer having availability (e.g., due to a change in a machine or resource availability) based on IOT data or published capacity data.

Accordingly, smart routing adjustment operations can include an adjustment of couriers, a notification to stakeholders, and other such adjustments. Furthermore, in an aspect, smart routing determinations can be performed by smart router module based on a difference between an estimated time of manufacturing and a planned time for manufacturing (e.g., if the difference is greater than a predetermined threshold difference, then a routing adjustment mechanism can occur). In another aspect, an intermediate product can be routed (e.g., based on a determined route adjustment by smart router module) to another manufacturing site (e.g., based on site proximity) based on a machine not working or labor shortage, or other such insight generated from the data. In another aspect, smart router module can select an optimal courier with a target route based on historical data, courier performance history, pricing data, weather conditions, and other such information.

In another aspect, individualized medicine platform module 106 can acquire manufacturing site data on a continual basis and smart router module can employ machine learning algorithms to determine optimized routes to perform manufacturing tasks based on a set of customized parameters. In another aspect, individualized medicine platform module 106 can employ notification module to transmit notifications to stakeholders based on re-scheduling tasks or route adjustments. Furthermore, in an aspect, blockchain 320 can store (on independent decentralized machines in a non-limiting embodiment) real-time data generated by individualized medicine platform module 106. Furthermore, in an aspect, programmatic logic code representing scheduling decisions and smart contracts between stakeholders can be stored on blockchain 320. In yet another aspect, routing determinations and data acquisition tasks can operate in connection with internet of things devices. For instance, individualized medicine platform module 106 can execute capacity decisions based on machine data, detect of machine malfunction and rerouting tasks, predictive analytics related to machine malfunctions.

In yet another aspect, each manufacturing facility or machines at a manufacturing facility can publish capacity data to its own respective blockchain 320. Furthermore, in a non-limiting embodiment, a center of excellence can publish its data (e.g., scheduling data, sample preparation data, etc.) to a COE-specific blockchain to store respective data (e.g., patient history data, real world evidence data, patient cellular and genetic therapies (CGT) journey data, etc.). Furthermore, smart contract logic code can be stored within each blockchain 320 and be executed based on events by the stakeholders. In another aspect, smart contracts can be executed between couriers and centers of excellence based on events published to the center of excellence blockchains.

Figure 4A:
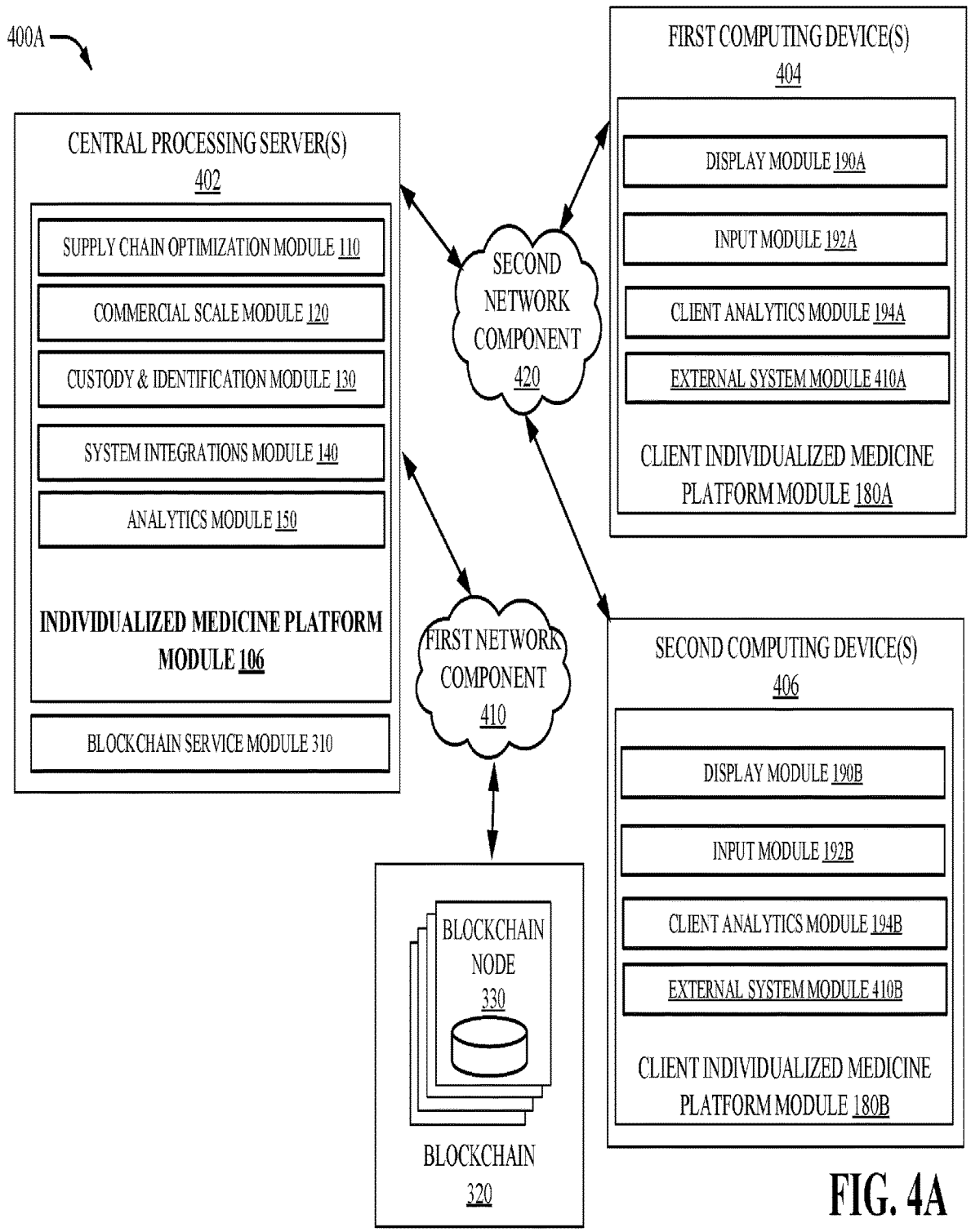
FIG. 4A illustrates an example, non-limiting system that includes a personalized medicine supply chain system configured as a central service provider interfacing with a blockchain system in accordance with one or more embodiments described herein.

FIG. 4A illustrates an example, non-limiting system 400A that includes a personalized medicine supply chain system configured as a central service provider interfacing with a blockchain system in accordance with one or more embodiments described herein. In various implementations, the example described with respect to FIG. 2 can be considered a continuation of the example describe in FIG. 1A. In an aspect, FIG. 2 illustrates an example, non-limiting environment 200 in which cloud-based services can be used to provide features corresponding to events and activities associated with a personalized medicine supply chain in accordance with one or more embodiments described herein. In an aspect, environment 200 can include server device(s) 102, computing device(s) 104, and network component 114, where computing device(s) 104 includes a processing system 230, and one or more computer-readable media 240. Repetitive description of like elements employed in other embodiments described herein is omitted for sake of brevity.

In some non-limiting embodiments, the systems disclosed in environment 100A of FIG. 1A and environment 200 of FIG. 2 can be configured to communicate and/or integrate with a distributed blockchain system (disclosed in FIG. 3) comprising multiple computing nodes, such that each computing node is configured to store a copy or a portion of a transaction data record on blockchain 320. In an aspect, blockchain 320 can be a public blockchain (e.g., every participant has a copy of an entire chain) or a private blockchain (e.g., every participant has access to a copy of the entire chain, however, a central authority can control via access settings the participants authorized to join the private network). As such, in a non-limiting embodiment, system 400A can comprise an individualized medicine platform module 106 executing on central server provider device(s) 402 that is configured to execute tasks on behalf of itself and other external systems.

As such, in some non-limiting embodiments, central server provider device(s) 402 (which comprises all the modules and functionality of server device(s) 102) is the only authority that can write (e.g., store its own data and data acquired from external sources) to blockchain 320. Thus, various stakeholders (e.g., manufacturers, couriers, collection centers, administrative manager, physicians, patients, payers, etc.) that utilize individualized medicine platform module 106 by integrating data from other systems (e.g., QMS, EMS, CMS, COP's, PMS, eCOA, etc.) to individualized medicine platform module 106 can allow individualized medicine platform module 106 to write integrated data to blockchain 320.

For instance, external service provider device(s) 404 (which comprises all the modules and functionality of computing device(s) 104) can further comprise external integration module 410A capable of transmitting data from an external data store (e.g., ERP, IVIES, LIMS, patient management system, courier management system, QMS, eCOA, etc.) to central service provider device(s) 402. In another instance, external service provider device(s) 406 (which comprises all the modules and functionality of computing device(s) 104) can further comprise external integration module 410B capable of transmitting data from an external data store (e.g., ERP, IVIES, LIMS, QMS, etc.), that is different than the external data store of service provider device(s) 404, to central service provider device(s) 402.

Accordingly, central service provider device(s) 402 can receive respective data from external service provider device (s) 404 and 406, and write some or all of the received data to blockchain 320. As such, external service provider device (s) 404 and 406 indirectly write data to blockchain 320 through central service provider device(s) 402 as a central authority. In an aspect, display module 190A and 190B, input module 192A, client analytics module 410A have at least the same functionality as the modules of computing device(s) 104. Also, in a non-limiting embodiment, one or more of external service provider device(s) 404 and 406 can be a server device storing the external data. In an aspect, system 400A can employ a first network component 410 that facilitates communication between blockchain 320 and central service provider device 402 and a second network component 420 that facilitates communication between central service provider device(s) 402 and external service provider device(s) 404 and 406. In an aspect, first network component 410 and second network component 420 can comprise at least the same functionality as network component 114.

In an aspect, individualized medicine platform module 106 can be configured as the central authority to write data (including integrated data from third party systems integrated with individualized medicine platform module 106) to blockchain 320. As such, individualized medicine platform module 106 can provide access to a primary transaction record stored on blockchain 320 to which any stakeholders can execute smart contracts, perform chain of identity data audits, perform chain of custody data audits, and/or generally access records. In yet another aspect, individualized medicine platform module 106 can provide access to more than one blockchain 320. For instance, a first blockchain can store only transaction data associated with courier events and a second blockchain can store only transaction data associated with manufacturing events such that relevant stakeholder devices can access respective blockchains.

Furthermore, encryption mechanisms can be provided to allow access to only authorized data on the immutable blockchain based on authorization credentials. As a non-limiting example, a stakeholder device utilizing individualized medicine platform module 106 can read data stored on blockchain 320 and the individualized medicine platform module 106 can write data to the blockchain 320 (e.g., append data to the blockchain 320). In yet another aspect, a node on the blockchain 320 can validate or remove transactions deemed to be invalid as well as determine an ordering of remaining valid transactions to be appended to the blockchain 320 as part of a new block. In an aspect, upon the generation of a new block (e.g., that has been validated), the data within the new block is immutable (e.g., cannot be modified or altered). In a non-limiting embodiment, one or more validation nodes associated with blockchain 320 can be validated in accordance with validation rules stored within the validation nodes, such rules including syntax requirements of data, specification of events or tasks a data contributor to the blockchain can perform, and other such rules. In a non-limiting embodiment, individualized medicine platform module 106 can configure the validation nodes and set of rules.

Figure 4B:
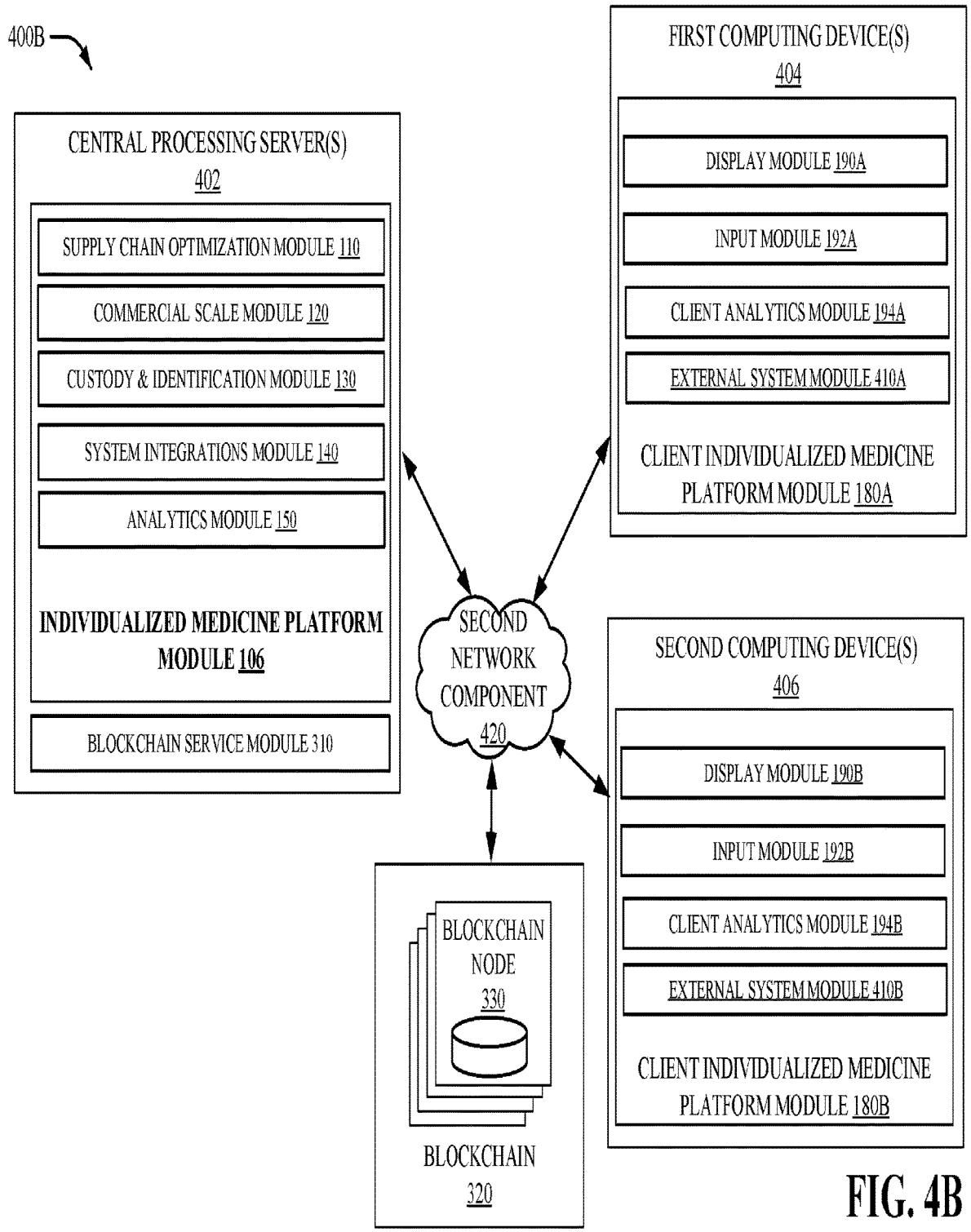
FIG. 4B illustrates an example, non-limiting system that includes a personalized medicine supply chain system and one or more distributed external system(s) directly interfacing with a blockchain system in accordance with one or more embodiments described herein.

Turning now to FIG. 4B illustrated is an example, non-limiting system 400B that includes a personalized medicine supply chain system and one or more distributed external system(s) directly interfacing with a blockchain system in accordance with one or more embodiments described herein. In various implementations, the example described with respect to FIG. 2 can be considered a continuation of the example describe in FIG. 1A. In an aspect, FIG. 2 illustrates an example, non-limiting environment 200 in which cloud-based services can be used to provide features corresponding to events and activities associated with a personalized medicine supply chain in accordance with one or more embodiments described herein. In an aspect, environment 200 can include server device(s) 102, computing device(s) 104, and network component 114, where computing device(s) 104 includes a processing system 230, and one or more computer-readable media 240. Repetitive description of like elements employed in other embodiments described herein is omitted for sake of brevity.

In some non-limiting embodiments, the systems disclosed in environment 100A of FIG. 1A and environment 200 of FIG. 2 can be configured to communicate and/or integrate with a distributed blockchain system (disclosed in FIG. 3) comprising multiple computing nodes, such that each computing node is configured to store a copy or a portion of a blockchain 320. In an aspect, blockchain 320 can be a public blockchain (e.g., every participant has a copy of an entire chain) or a private blockchain (e.g., every participant has access to a copy of the entire chain, however, a central authority can control via access settings the participants authorized to join the private network). As such, in a non-limiting embodiment, individualized medicine platform module 106 executing on server device(s) 102 is one decentralized authority that can write to blockchain 320. Furthermore, various stakeholders (e.g., manufacturers, couriers, collection centers, administrative manager, physicians, patients, payers, etc.) using external service provider device 404 and/or 406 can utilize the functionality and features of individualized medicine platform module 106 (e.g., generate analytics, organize data, access data, etc.) as well as integrate external data from external systems (e.g., QMS, EMS, CMS, COP's, PMS, eCOA, etc.) with individualized medicine platform module 106, but can also directly write external data (e.g., store data representing transactions, events, information, etc.) to blockchain 320.

Furthermore, in an aspect, individualized medicine platform module 106 can be configured as one of many authorities permitted to write data (including integrated data from third party systems integrated with individualized medicine platform module 106) to blockchain 320. Furthermore, as such, individualized medicine platform module 106 and external service provider device(s) 404 and 406 can access the primary transaction record stored on blockchain 320 to which any stakeholders can execute smart contracts, perform chain of identity data audits, perform chain of custody data audits, and/or generally access records. In yet another non-limiting embodiment, individualized medicine platform module 106 and respective system integrators (e.g., stakeholder devices) can access one or more respective blockchain 320 based on the type of transactions, events or information stored on each respective blockchain. For instance, a first blockchain can store only transaction data associated with courier events and a second blockchain can store only transaction data associated with manufacturing events such that relevant stakeholder devices can access respective blockchains. In an aspect, non-limiting data stored on the blockchain or on data stores coupled to server device(s) 102 can include identity data, custody data, label data (e.g., on samples, materials, etc.), scheduling data (e.g., between supply chain stakeholders), workflow data, analytics feeder data, integration data, asset data, financial data, laboratory data, manufacturing data human resource data, inventory data, patient compliance data, patient enrollment data, patient information (e.g., consent data), patient identifier data, validation data, audit data, shipment data, patient outcome data, clinic outcome data, payment data (e.g., reimbursement payments), and/or tracking data (e.g., product tracking).

Furthermore, in some non-limiting embodiments, encryption mechanisms can be provided to allow access to only authorized data on the immutable blockchain based on authorization credentials. As a non-limiting example, a third-party system and individualized medicine platform module 106 can read data stored on and/or write data to the blockchain 320 (e.g., append data to the blockchain 320). In yet another aspect, one or more node on the blockchain 320 can validate or remove transactions deemed to be invalid as well as determine an ordering of remaining valid transactions to be appended to the blockchain 320 as part of a new block. In an aspect, upon the generation of a new block (e.g., that has been validated), the data within the new block is immutable (e.g., cannot be modified or altered). In another aspect, the validation of data to be appended into a proposed new block can be validated based on a determination by third parties and individualized medicine platform module 106 (e.g., a consensus determination that a transaction complies with rules of blockchain 320). In a non-limiting embodiment, one or more validation nodes associated with blockchain 320 can be validated in accordance with validation rules stored within the validation nodes, such rules including syntax requirements of data, specification of events or tasks a data contributor to the blockchain can perform, and other such rules. In a non-limiting embodiment, individualized medicine platform module 106 and other stakeholder devices can configure the validation nodes and set of rules.

In some implementations, blockchain 320 can be configured as a shared database between third party systems and individualized medicine platform module 160. As such, the blockchain 320 can act as a shared ledger of transactional events within an entire individualized medicine supply chain. Furthermore, individualized medicine platform module 160 can trigger notification data based on triggering event data or transactional data being appended to blockchain 320 by third party systems and/or individualized medicine platform module 160. For instance, if a manufacturer device appends data (e.g., from an enterprise manufacturing system) to blockchain 320 that indicates manufacturing capacity has decreased by 50% due to a machine malfunction, then a notification can be triggered (e.g., based on receipt of data indicating change in capacity above a threshold capacity) based on the capacity change event, such that individualized medicine platform module 160 can perform a re-routing and rescheduling task of the product to be manufactured elsewhere.

Figure 5:
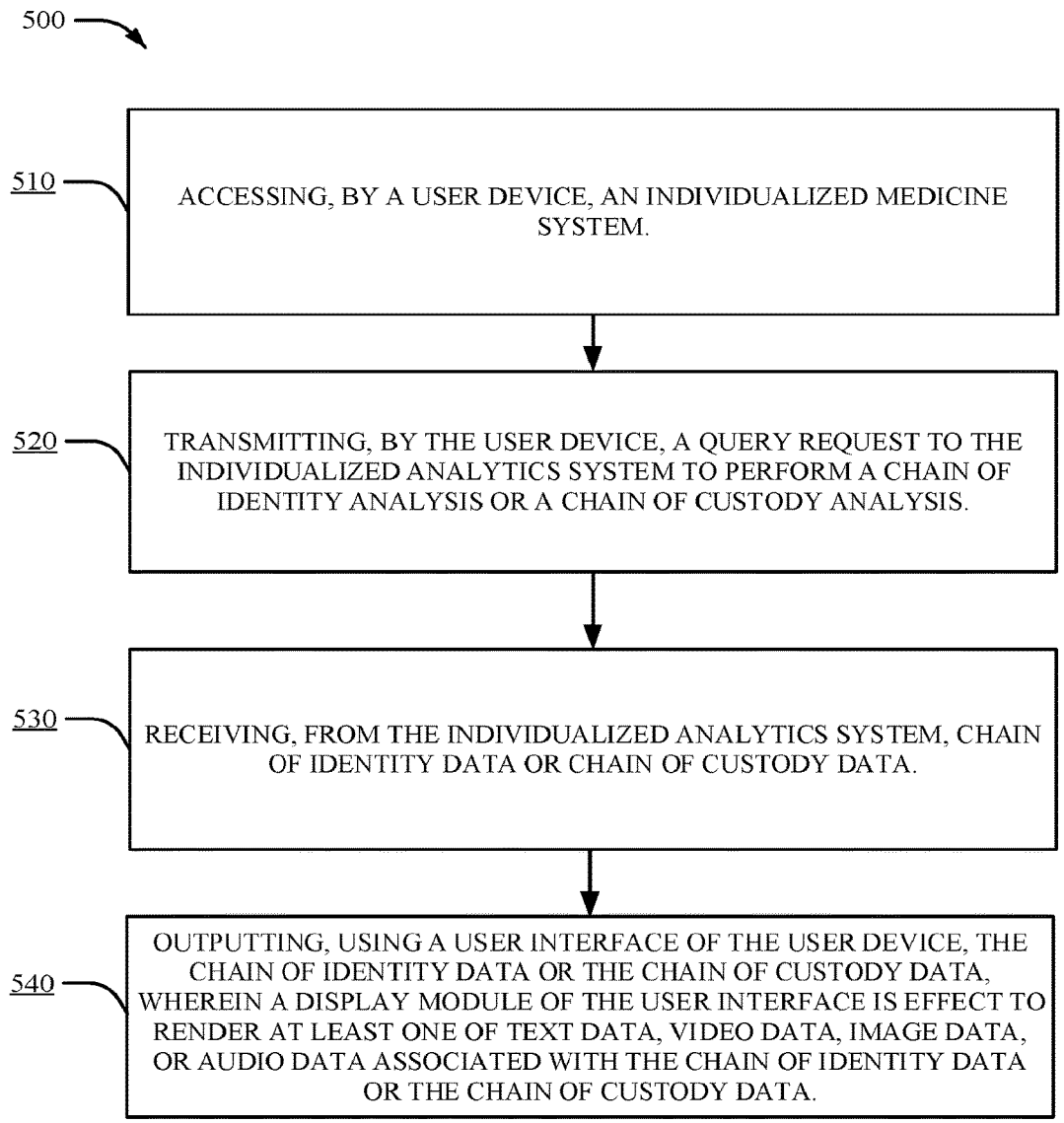
FIG. 5 illustrates a flow diagram of an example, non-limiting computer-implemented method that can facilitate a storing and querying of data associated with a personalized medicine supply chain on a block chain in accordance with one or more embodiments described herein.

FIG. 5 illustrates a flow diagram of an example, non-limiting computer-implemented method 500 that facilitates an outputting of chain of identity or chain of custody data from one or more node of a blockchain. In an aspect, one or more of the components described in computer-implemented method 500 can be electrically and/or communicatively coupled to one or more devices. Repetitive description of like elements employed in other embodiments described herein is omitted for sake of brevity.

In some implementations, at reference numeral 510, a user device accesses an individualized medicine system operatively coupled to a processor. At reference numeral 520, the user device transmits a query request to the individualized analytics system to perform a chain of identity analysis or chain of custody analysis. At reference numeral 530, the user device receives, from the individualized analytics system, chain of identity data or chain of custody data. At reference numeral 540, the user interface of the user device outputs the chain of identity data or the chain of custody data, wherein a display module of the user interface is effective to render at least one of text data, video data, image data, or audio data associated with the chain of identity data or the chain of custody data.

Figure 6:
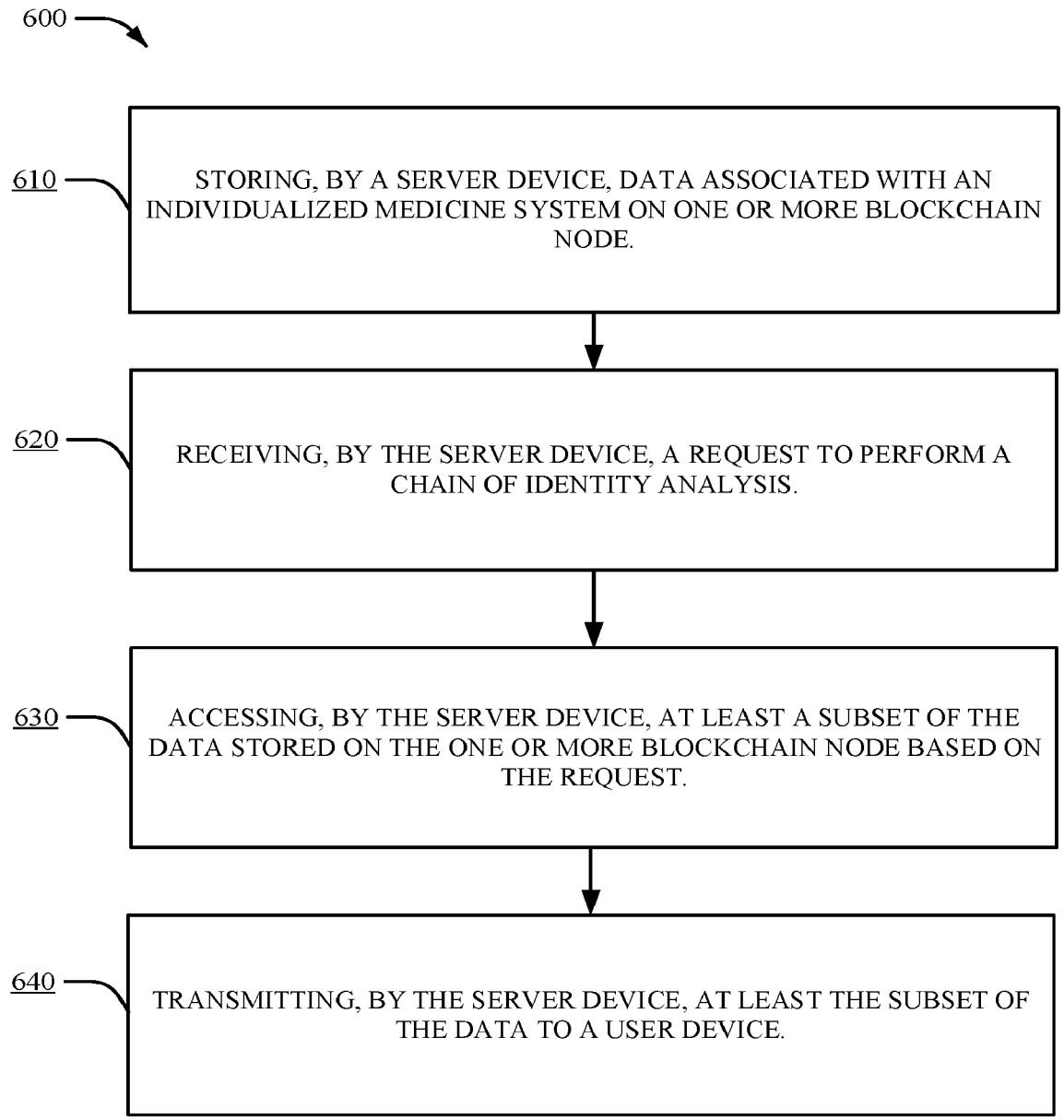
FIG. 6 illustrates a flow diagram of an example, non-limiting computer-implemented method that can facilitate a storing and querying of data associated with a personalized medicine supply chain on a block chain in accordance with one or more embodiments described herein.

FIG. 6 illustrates a flow diagram of an example, non-limiting computer-implemented method 600 that facilitates an outputting of chain of identity or chain of custody data from one or more node of a blockchain. In an aspect, one or more of the components described in computer-implemented method 600 can be electrically and/or communicatively coupled to one or more devices. Repetitive description of like elements employed in other embodiments described herein is omitted for sake of brevity.

In some implementations, at reference numeral 610, a server device stores data associated with an individualized medicine system operatively coupled to a processor on one or more blockchain node. At reference numeral 620, the server device receives a request to perform a chain of identity analysis or chain of custody analysis. At reference numeral 630, the server device accesses at least a subset of the data stored on the one or more blockchain node based on the request. At reference numeral 640, the server device transmits at least the subset of the data to a user device.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

We claim:

1. A computer-implemented method for monitoring chain of custody and chain of identity for a patient sample, intermediate product, or final product in a personalized medicine supply chain, the method comprising:
   acquiring, by a server comprising one or more processors and configured to execute instructions for a personalized medicine supply chain platform, event data corresponding to the personalized medicine supply chain that is associated with one or more of patient enrollment, patient sample collection, product manufacturing, material or product shipping, and personalized medicine infusion;
   curating, by the server, the event data to determine one or more of (i) event identifier data associated with a task in a supply chain event, (ii) time data associated with when the task of the supply chain event occurred, (iii) identity data associated with an identity of an entity or custodian associated with the task of the supply chain event, (iv) description data including information about the task of the supply chain event, or (v) location data associated with where the task of the supply chain event occurred;
   analyzing, by the server, the curated event data to determine transactional processes and identify custody transfer information and custodian identity information for the patient sample, intermediate product, or final product in the personalized medicine supply chain; and
   generating, by the server, audit data representing an audit trail of the one or both of the chain of custody and the chain of identity based on the determined transactional processes and identified custody transfer information and custodian identity information.

2. The computer-implemented method of claim 1 wherein:
   the chain of custody includes data associated with a custody transfer of the patient sample, intermediate product, or final product in a completed personalized therapy or an unfinished personalized therapy; and
   the chain of identity includes data associated with a change of custodial identity of the patient sample, intermediate product, or final product in a completed personalized therapy or an unfinished personalized therapy.

3. The computer-implemented method of claim 1 wherein the audit data representing an audit trail of one or both of the chain of custody and the chain of identity corresponds to each leg of a journey undertaken by the patient sample, the intermediate product, or the final product in the personalized medicine supply chain.

4. The computer-implemented method of claim 1 wherein the description data includes information pertaining to the task comprising at least one of (i) a verification of a patient, (ii) a scanning of a label on the patient sample, the intermediate product, or the final product, (iii) a verification that a label matched an identifier number, (iv) a verification that an apheresis occurred, or (v) a transfer of a material from one entity to another entity.

5. The computer-implemented method of claim 1, further comprising:
   receiving, by the server, a request for a personalized therapy order from a first computing device executing a personalized medicine application associated with the personalized medicine supply chain platform; and
   authenticating identity information associated with a user of the personalized medicine application on the first computing device based on a set of user criteria including user identity permissions and user roles permissions.

6. The computer-implemented method of claim 5 wherein the authenticating comprises:
   employing an authentication federation scheme operable to authenticate user profiles associated with the personalized medicine application, and generating an access token for access by authentication server devices different from the server configured to execute instructions for the personalized medicine supply chain platform.

7. The computer-implemented method of claim 1, further comprising:
generating identity data corresponding to one or more user profiles of a personalized medicine application associated with the personalized medicine supply chain platform;
generating a role corresponding to the one or more user profiles, wherein the role comprises at least one regional requirement and at least one therapy type; and
assigning a group of permissions to the role, wherein the group of permissions comprises a defined permitted action for execution by an authenticated user profile and a defined resource corresponding to the defined permitted action, wherein a data store, executing on the server, stores at least one of the identity data, the role, the group of permissions, or grant data, and wherein the grant data represents an effective date associated with a grant of the defined permission.

8. The computer-implemented method of claim 1, further comprising:
generating identity data corresponding to one or more user profiles of a personalized medicine application associated with the personalized medicine supply chain platform;
generating a role corresponding to the one or more user profiles, wherein the role comprises at least one regional requirement and at least one therapy type; and
assigning a group of permissions to the role, wherein the group of permissions comprises a defined permitted action for execution by an authenticated user profile and a defined resource corresponding to the defined permitted action, wherein the defined permitted action comprises one or more of generating a user profile credential, assigning a user profile to a group of permissions, or requesting an authentication operation.

9. The computer-implemented method of claim 8, further comprising:
generating and transmitting, by the server, a therapy order request to a second computing device corresponding to a manufacturing site scheduler; and
receiving, by the server, an approved therapy order request from the second computing device.

10. The computer-implemented method of claim 9, further comprising:
generating and/or storing location data associated with an ordered patient sample to allow for traceability of the patient sample, the intermediate product, or the final product.

11. The computer-implemented method of claim 1 wherein the personalized medicine supply chain platform is in communication or integrated with a distributed blockchain system comprising multiple computing nodes configured to store a copy or at least a portion of data on a blockchain.

12. The computer-implemented method of claim 11 wherein one or both of the chain of identity data and the chain of custody data is stored on the blockchain, and wherein the method further comprises:
storing, on one or more blockchain nodes of the blockchain, a set of verifiable and immutable transactions associated with chain of custody event data or chain of identity event data.

13. The computer-implemented method of claim 11 wherein the audit data is stored on the blockchain.

14. The computer-implemented method of claim 1, further comprising:
receiving, by the server, a request to perform an analysis on one or both of the chain of custody and the chain of identity for the patient sample, intermediate product, or final product in the personalized medicine supply chain.

15. A system for a personalized medicine supply chain platform, comprising:
at least one processor; and
a non-transitory memory including processor executable code, wherein the processor executable code upon execution by the at least one processor causes the at least one processor to monitor chain of custody and chain of identity for a patient sample, intermediate product, or final product in a personalized medicine supply chain, by performing operations comprising:
acquiring event data corresponding to the personalized medicine supply chain that is associated with one or more of patient enrollment, patient sample collection, product manufacturing, material or product shipping, and personalized medicine infusion;
curating the event data to determine one or more of (i) event identifier data associated with a task in a supply chain event, (ii) time data associated with when the task of the supply chain event occurred, (iii) identity data associated with an identity of an entity or custodian associated with the task of the supply chain event, (iv) description data including information about the task of the supply chain event, or (v) location data associated with where the task of the supply chain event occurred;
analyzing the curated event data to determine transactional processes and identify custody transfer information and custodian identity information for the patient sample, intermediate product, or final product in the personalized medicine supply chain; and
generating audit data representing an audit trail of the one or both of the chain of custody and the chain of identity based on the determined transactional processes and identified custody transfer information and custodian identity information.

16. The system of claim 15 wherein:
the chain of custody includes data associated with a custody transfer of the patient sample, intermediate product, or final product in a completed personalized therapy or an unfinished personalized therapy; and
the chain of identity includes data associated with a change of custodial identity of the patient sample, intermediate product, or final product in a completed personalized therapy or an unfinished personalized therapy.

17. The system of claim 15 wherein the audit data representing an audit trail of one or both of the chain of custody and the chain of identity corresponds to each leg of a journey undertaken by the patient sample, the intermediate product, or the final product in the personalized medicine supply chain.

18. The system of claim 15 wherein the description data includes information pertaining to the task comprising at least one of (i) a verification of a patient, (ii) a scanning of a label on the patient sample, the intermediate product, or the final product, (iii) a verification that a label matched an identifier number, (iv) a verification that an apheresis occurred, or (v) a transfer of a material from one entity to another entity.

19. The system of claim 15 wherein the processor executable code, upon execution by the at least one processor, causes the at least one processor to monitor chain of custody and chain of identity by:
receiving a request for a personalized therapy order from a first computing device executing a personalized medicine application associated with the personalized medicine supply chain platform; and
authenticating identity information associated with a user of the personalized medicine application on the first computing device based on a set of user criteria including user identity permissions and user roles permissions.

20. The system of claim 19 wherein the authenticating comprises:
employing an authentication federation scheme operable to authenticate user profiles associated with the personalized medicine application, and
generating an access token for access by one or more authentication server devices different from a server comprising the at least one processor configured to execute instructions for the personalized medicine supply chain platform.

21. The system of claim 15 wherein the processor executable code, upon execution by the at least one processor, causes the at least one processor to monitor chain of custody and chain of identity by:
generating identity data corresponding to one or more user profiles of a personalized medicine application associated with the personalized medicine supply chain platform;
generating a role corresponding to the one or more user profiles, wherein the role comprises at least one regional requirement and at least one therapy type; and
assigning a group of permissions to the role, wherein the group of permissions comprises a defined permitted action for execution by an authenticated user profile and a defined resource corresponding to the defined permitted action, wherein a data store of the system, in communication with the at least one processor, stores at least one of the identity data, the role, the group of permissions, or grant data, and wherein the grant data represents an effective date associated with a grant of the defined permission.

22. The system of claim 15 wherein the processor executable code, upon execution by the at least one processor, causes the at least one processor to monitor chain of custody and chain of identity by:
generating identity data corresponding to one or more user profiles of a personalized medicine application associated with the personalized medicine supply chain platform;
generating a role corresponding to the one or more user profiles, wherein the role comprises at least one regional requirement and at least one therapy type; and
assigning a group of permissions to the role, wherein the group of permissions comprises a defined permitted action for execution by an authenticated user profile and a defined resource corresponding to the defined permitted action, wherein the defined permitted action comprises one or more of generating a user profile credential, assigning a user profile to a group of permissions, or requesting an authentication operation.

23. The system of claim 22 wherein the processor executable code, upon execution by the at least one processor, causes the at least one processor to monitor chain of custody and chain of identity by:
generating and transmitting a therapy order request to a second computing device corresponding to a manufacturing site scheduler; and
receiving an approved therapy order request from the second computing device.

24. The system of claim 23 wherein the processor executable code, upon execution by the at least one processor, causes the at least one processor to monitor chain of custody and chain of identity by:
generating and/or storing location data associated with an ordered patient sample to allow for traceability of the patient sample, the intermediate product, or the final product.

25. The system of claim 15 wherein the personalized medicine supply chain platform is in communication or integrated with a distributed blockchain system comprising multiple computing nodes configured to store a copy or at least a portion of data on a blockchain.

26. The system of claim 25 wherein one or both of the chain of identity data and the chain of custody data is stored on the blockchain, and wherein the method further comprises:
storing, on one or more blockchain nodes of the blockchain, a set of verifiable and immutable transactions associated with chain of custody event data or chain of identity event data.

27. The system of claim 25 wherein the audit data is stored on the blockchain.

28. The system of claim 15 wherein the processor executable code, upon execution by the at least one processor, causes the at least one processor to monitor chain of custody and chain of identity by:
receiving a request to perform an analysis on one or both of the chain of custody and the chain of identity for the patient sample, intermediate product, or final product in the personalized medicine supply chain.

29. A non-transitory, computer-readable medium storing instructions thereon that, when executed by one or more processors of a computing system, cause the computing system to perform operations for monitoring chain of custody and chain of identity for a patient sample, intermediate product, or final product in a personalized medicine supply chain, comprising:
acquiring, by a server comprising one or more processors and configured to execute instructions for a personalized medicine supply chain platform, event data corresponding to the personalized medicine supply chain that is associated with one or more of patient enrollment, patient sample collection, product manufacturing, material or product shipping, and personalized medicine infusion;
curating, by the server, the event data to determine one or more of (i) event identifier data associated with a task in a supply chain event, (ii) time data associated with when the task of the supply chain event occurred, (iii) identity data associated with an identity of an entity or custodian associated with the task of the supply chain event, (iv) description data including information about the task of the supply chain event, or (v) location data associated with where the task of the supply chain event occurred;
analyzing, by the server, the curated event data to determine transactional processes and identify custody transfer information and custodian identity information for the patient sample, intermediate product, or final product in the personalized medicine supply chain; and generating, by the server, audit data representing an audit trail of the one or both of the chain of custody and the chain of identity based on the determined transactional processes and identified custody transfer information and custodian identity information.

\* \* \* \* \*